US 11,565,100 B2

(12) United States Patent
Cowe

(10) Patent No.: US 11,565,100 B2
(45) Date of Patent: Jan. 31, 2023

(54) APPARATUS FOR TRANSDERMAL MEDICAMENT DELIVERY

(71) Applicant: Owen Mumford Limited, Oxford (GB)

(72) Inventor: Toby Cowe, Oxfordshire (GB)

(73) Assignee: Owen Mumford Limited, Oxfordshire (GB)

(*) Notice: Subject to any disclaimer, the term of this patent is extended or adjusted under 35 U.S.C. 154(b) by 1249 days.

(21) Appl. No.: 15/770,650

(22) PCT Filed: Nov. 23, 2016

(86) PCT No.: PCT/GB2016/053667
§ 371 (c)(1),
(2) Date: Apr. 24, 2018

(87) PCT Pub. No.: WO2017/089785
PCT Pub. Date: Jun. 1, 2017

(65) Prior Publication Data
US 2018/0311487 A1  Nov. 1, 2018

(30) Foreign Application Priority Data
Nov. 23, 2015  (GB) .................................... 1520653

(51) Int. Cl.
*A61M 37/00* (2006.01)
(52) U.S. Cl.
CPC . *A61M 37/0092* (2013.01); *A61M 2037/0007* (2013.01); *A61M 2210/04* (2013.01)
(58) Field of Classification Search
CPC .............. A61M 37/00; A61M 37/0092; A61M 2037/0007; A61M 2210/04; A61M 2037/007; A61K 41/0047; A61N 1/325
See application file for complete search history.

(56) References Cited

U.S. PATENT DOCUMENTS

| 4,003,382 | A | * | 1/1977 | Dyke | ................... A61M 25/10 604/103 |
| 5,267,985 | A | | 12/1993 | Shimada et al. | |
| 5,617,851 | A | | 4/1997 | Lipkovker | |
| 6,322,532 | B1 | | 11/2001 | D'Sa et al. | |

(Continued)

FOREIGN PATENT DOCUMENTS

| WO | WO 97/10023 A2 | 3/1997 |
| WO | WO 2007/028114 A2 | 3/2007 |

OTHER PUBLICATIONS

Apr. 4, 2017 Transmittal of ISR and Written Opinion of Int'l Searching Authority for PCT/GB2016/053667.

*Primary Examiner* — Tiffany Legette
(74) *Attorney, Agent, or Firm* — Quarles & Brady LLP

(57) ABSTRACT

A container (200) for containing a coupling medium for transdermal delivery of a medicament and a transducer unit (100) for use with the container (200) are disclosed. The transducer unit (100) has a transducer (108) with an output face (110), and the container comprises a chamber (214) for receiving the coupling medium and a contact surface (212) for contacting the output face (110) of the transducer (108). The container (200) is attachable to the transducer unit (100) and is arranged such that, upon attachment of the container (200) to the transducer unit (100), an acoustic coupling for ultrasound transmission is formed between the output face (110) of the transducer (108) and the contact surface (212).

46 Claims, 13 Drawing Sheets

(56) References Cited

U.S. PATENT DOCUMENTS

| | | |
|---|---|---|
| 6,650,935 B1 | 11/2003 | Watmough |
| 2002/0138037 A1 | 9/2002 | Weimann |
| 2007/0088297 A1* | 4/2007 | Redding ........... A61M 37/0092 |
| | | 604/289 |
| 2008/0215039 A1* | 9/2008 | Slatkine ................ A61M 5/425 |
| | | 606/9 |
| 2009/0124959 A1 | 5/2009 | Pelzer |
| 2015/0018752 A1 | 1/2015 | Unger et al. |
| 2015/0025420 A1* | 1/2015 | Slayton ................ A61B 18/203 |
| | | 601/2 |
| 2015/0045723 A1 | 2/2015 | Paithankar et al. |

* cited by examiner

APPARATUS FOR TRANSDERMAL MEDICAMENT DELIVERY

The present application is a § 371 submission of international application no. PCT/GB2016/053667, filed 23 Nov. 2016 and titled Apparatus for Transdermal Medicament Delivery, which was published in the English language on 1 Jun. 2017 with publication no. WO 2017/089785 A1, and which claims the benefit of the filing date of GB 15 20653.5 filed 23 Nov. 2015, the contents of which are incorporated herein by reference.

The present invention relates to apparatus for medicament delivery. In particular, but not exclusively, the invention relates to transducer units for needle-free transdermal delivery of medicament and to containers for use with the transducer units.

Some medicaments, such as insulin for the treatment of diabetes mellitus, are most effectively administered subcutaneously. Traditionally, subcutaneous administration is achieved using a needle to pierce the natural barrier of the skin to provide a pathway for hypodermic injection of the medicament.

Ultrasound-assisted medicament delivery, known as sonophoresis, has been proposed as an alternative method for transdermal delivery of medicaments. In sonophoresis, a coupling medium (typically a liquid or gel) is applied to the skin. The coupling medium is then excited by an ultrasonic transducer. Application of ultrasonic energy to the skin, by way of the coupling medium, results in a temporary increase in the permeability of the skin. This can be exploited for medicament delivery either by applying a medicament to the skin after sonophoresis or, more conveniently, by incorporating the medicament in the coupling medium (for example by dissolution or suspension) so that delivery is simultaneous with sonophoresis.

It is believed that more than one mechanism may contribute to the increase in permeability of the skin. However, it has been shown that the amount of medicament delivered during simultaneous sonophoresis is dependent on the amount of acoustic cavitation that occurs in the coupling medium. It is believed that the collapse of cavitation bubbles results in the formation of microjets in the coupling medium, and that the microjets provide a transport mechanism for delivery of the medicament through the skin.

FIG. 1 of the accompanying drawings is a schematic illustration of medicament delivery using simultaneous sonophoresis. A coupling medium 10 is placed on the recipient's skin 12. The coupling medium 10 is loaded with the medicament to be delivered. An ultrasonic transducer 14 is positioned with an output face 16 of the transducer 14 in acoustic contact with the coupling medium 10. The ultrasonic transducer is energised by a signal source 18. Ultrasonic vibrations are transferred to the coupling medium 10 by way of the output face 16. The vibrations permeate through the coupling medium 10 towards the skin. Due to attenuation effects, the intensity of the vibrations is at an effective level only within an envelope 20. A focusing zone 22, in which the vibrations are most intense, lies within the envelope 20. Cavitation and microjet formation occurs in the focusing zone 22. Microjets are directed towards the skin 12 over a treatment area with diameter D. The microjets penetrate the skin 12 in this region, resulting in transport of the medicament across the skin barrier. It will be appreciated that the shape and position of the focusing zone 22 and the envelope 20 will depend on a multitude of factors and can be considerably more complex than shown in FIG. 1.

Ultrasound-assisted medicament delivery using sonophoresis is considered to be less painful and less invasive, and to carry a reduced likelihood of infection, compared with hypodermic injection using needles. However, for effective medicament delivery using sonophoresis, it is necessary to ensure good acoustic transmission from the ultrasound transducer to the coupling medium to allow effective stimulation of the coupling medium. It is also important to achieve good coupling between the coupling medium and the skin, to allow transport of medicament from the coupling medium into the skin, to ensure that the coupling medium remains sterile. These and other factors have so far limited the use of sonophoresis largely to clinical environments using specialised apparatus operable only by trained personnel. It would however be desirable to provide practical devices that can be used for self-administration of medicaments outside of a clinical environment, and it is against this background that the present invention has been devised.

From a first aspect of the present invention, there is provided a container for containing a coupling medium for transdermal delivery of a medicament using a transducer unit having a transducer with an output face. The container comprises a contact surface for contacting the output face of the transducer, and a chamber for receiving the coupling medium. The container is attachable to the transducer unit and is arranged such that, upon attachment of the container to the transducer unit, an acoustic coupling for ultrasound transmission is formed between the output face of the transducer and the contact surface.

By ensuring that an acoustic coupling is formed between the output face of the transducer and the contact surface, effective acoustic transmission through the interface between the transducer and the contact surface can be achieved. In this way, it is possible to ensure good acoustic transmission from the transducer to the chamber of the container, through the contact surface. Thus, with an appropriate contact medium in the chamber of the container, ultrasound transmission into the contact medium at an intensity suitable for ultrasound-assisted sonophoresis can be readily achieved.

The acoustic coupling between the output face of the transducer and the contact surface is formed upon attachment of the container to the transducer unit, so that special precautions are not required to achieve good acoustic transmission from the transducer to the coupling medium. Accordingly, when used with a suitable transducer unit, the container of the present invention can be used in a non-clinical environment and by untrained personnel, and in particular for self-administration of medicament.

The container may be arranged such that a substantially air-free coupling between the output face of the transducer and the contact surface is formed upon attachment of the container to the transducer unit. The absence of air from the interface between the output face and the contact surface helps to avoid attenuation or masking of acoustic transmission through the coupling.

Preferably, the contact surface is deformable to conform to the output face of the transducer upon attachment of the container to the transducer unit. In one embodiment, the contact surface is arranged such that a contact area between the contact surface and the output face increases progressively to exclude air during attachment of the container to the transducer unit. For example, the contact surface may comprise a convex surface for contact with the output face of the transducer. The contact surface may, for example, have a domed shape, with the apex of the dome projecting towards the transducer unit.

The container may comprise a contact membrane, and the contact surface may comprise a surface of the contact membrane. Preferably, the chamber is defined at least in part by the contact membrane. For example, the contact membrane may close a proximal end of the chamber.

The contact membrane may be flexible, and is preferably of an elastomeric material. For example, the contact membrane may comprise a silicone material. Preferably, the contact membrane is impedance matched to the coupling medium. In this way, acoustic attenuation at the interface between the contact membrane and the coupling medium is minimised, and so the output of the transducer is transferred to the coupling medium substantially as though no contact membrane were present. In this way, the contact membrane can be described as being acoustically transparent.

The contact membrane may be arranged to elastically deform upon attachment of the container to the transducer unit. If the container is releasable, the elastically deformed contact membrane may act to apply a force between the container and the transducer unit to aid release and ejection of the container.

The container may comprise a contact medium to couple the contact membrane to the output face of the transducer upon attachment of the container to the transducer unit. The contact medium facilitates the formation of the substantially air-free coupling between the contact membrane and the output face. The container may be provided with a removable seal arranged to contain the contact medium between the contact membrane and the seal. Preferably, the contact medium is a gel-type ultrasonic coupling medium.

The casing may be of a rigid plastics material. In this way, the casing can support a flexible contact membrane and/or a gel or liquid-like coupling medium. The container may include a liner for separating the coupling medium from the casing. The liner is preferably of an elastomeric material, such as a silicone rubber material. In a preferred embodiment, the contact membrane, when present, is part of the liner.

A least one portion of the casing may extend through the liner to attach the liner to the casing. For example, the liner may be overmoulded onto the casing. Alternatively, the liner and/or the membrane (when present) could be adhesively or otherwise attached to the casing.

The contact surface may be disposed at a proximal end of the chamber. An opposite, distal end of the chamber may be open to allow contact between the coupling medium and the skin of a user. Alternatively, the distal end of the chamber may be closed by a closure membrane. The closure membrane is preferably of a material that is normally impermeable to the coupling medium but becomes permeable under sonophoresis. Said another way, the closure membrane may be a material that is penetrable by ultrasonic activity. For example, the closure membrane may comprise a skin substitute material.

Suitable skin substitute materials include, but are not limited to: temporary impervious dressing materials, including single-layer materials such as Tegaderm (3M, St Paul, Minn., USA) and Opsite (Smith & Nephew plc, London, UK) and bi-layered tissue engineered materials such as TransCyte (Smith & Nephew plc, London, UK); single layer durable skin substitutes such as Alpigraft (Organogenesis Inc., Canton, Mass., USA); bovine or porcine collagen sheets; composite tissue engineered skin substitutes such as Integra (Integra LifeSciences Corporation, Plainsboro, N.J., USA) and Biobrane (Smith & Nephew plc, London, UK).

The closure membrane may define a concave surface at the distal end of the container. In this case, the closure membrane may have a radius of curvature that is equal to or larger than the radius of curvature of the contact surface, such that the closure membrane becomes flat or convex when the contact surface conforms to the shape of the output face of the transducer to aid contact between the closure membrane and the skin.

The distal end of the chamber may include a layer of relatively high-viscosity coupling medium. In particular, the distal end of the chamber may be closed by a self-supporting layer of the coupling medium. In that case, a closure member may not be present, to permit direct contact between the self-supporting layer of the coupling medium and the user's skin.

The chamber may be generally cylindrical. Alternatively, the chamber may have a non-uniform diameter. The chamber may be shaped to conform to the envelope of acoustic propagation from the transducer, so as to reduce the volume of coupling medium required to fill the chamber. In one example, the diameter of the chamber decreases with distance from the contact surface over at least a portion of the chamber. For example, the chamber may include a funnel-shaped portion or a frustoconical portion.

The chamber may contain a medicament-containing coupling medium. In this way, medicament can be transported through the user's skin with the coupling medium. In some embodiments, the medicament-containing coupling medium substantially fills the chamber.

The medicament may be uniformly distributed in the chamber. In other embodiments, the medicament is non-uniformly distributed in the chamber. For example, the medicament-containing coupling medium may be contained in a volume within the chamber. A further portion of the chamber, for example a remaining portion of the chamber, may contain a medicament-free coupling medium. In this way, the medicament can be positioned only where it will be subject to transport through the skin by sonophoresis. By distributing the medicament selectively in the chamber in this way, the amount of medicament required to deliver a given dose from the container can be reduced compared to arrangements in which the medicament is uniformly distributed in the chamber.

For example, the volume of medicament-containing coupling medium may be suspended in the medicament-free coupling medium or encapsulated by the medicament-free coupling medium. The medicament-containing coupling medium may be contained in a capsule suspended in the chamber. The capsule may be suspended in the chamber by one or more webs connected to the casing of the container or, when present, to the liner of the container. In another example, the medicament-containing coupling medium is disposed in a layer in the chamber. For instance, in one embodiment, the medicament-containing coupling medium is provided in an intermediate layer between two layers of medicament-free coupling medium.

At least one dividing membrane may be provided for containing the medicament-containing coupling medium within the volume. The dividing membrane is preferably impedance matched to the coupling medium. The dividing membrane may be of a material that is normally impermeable to the coupling medium but becomes permeable under sonophoresis to allow the medicament-containing coupling medium to pass out of the volume during sonophoresis. For example, the dividing membrane may be of a material penetrable by ultrasonic activity, such as a skin substitute material. If medicament transport across the dividing membrane is not required, the dividing membrane may be of a non-permeable material. In one embodiment, the dividing membrane comprises a silicone rubber. A plurality of dividing membranes of the same or different materials may be provided.

The coupling medium, or a portion of the coupling medium, may be transferred into the chamber or between portions of the chamber before use of the container in sonophoresis. For example, in one embodiment, attachment of the container to the transducer unit causes displacement of coupling medium from a reservoir portion of the chamber to an operating portion of the chamber. The operating portion of the chamber may be open at a distal end of the chamber, so that, when the coupling medium enters the operating portion of the chamber, the coupling medium flows into contact with the user's skin or flows outside the container to make contact with the user's skin. Conveniently, the transducer of the transducer unit may displace the coupling medium from the reservoir portion to the operating portion.

The reservoir portion and the operating portion may be separated by a separator membrane. The separator membrane is preferably impedance matched to the coupling medium. The separator membrane may be normally impermeable and may become permeable under the application of fluid pressure from the coupling medium. For example, the separator membrane may be of a perforated elastomeric material, such as a silicone rubber material.

In another embodiment, the container comprises a reservoir external to the chamber for holding coupling medium, and transfer means for transferring the coupling medium to the chamber. The reservoir may be connected to the chamber by a fluid connection. The transfer means may comprise a piston or plunger disposed in the reservoir.

The transfer means may be operable by a user of the device, for example upon activation of a button or other trigger device. Alternatively, operation of the transfer means may be automatic. By way of example, the container or the transducer unit may comprise skin contact detection means and the transfer means may be operable upon detection of skin contact by the skin contact detection means.

The container may further comprise engagement means for locking the container to the transducer unit. Preferably, the engagement means is arranged such that, upon attachment of the container to the transducer unit, the engagement means engages with the transducer unit once the coupling between the output face of the transducer and the contact surface has been formed. Upon engagement of the engagement means with the container, the contact surface may be pressed against the output face of the transducer.

The engagement means may comprise an engagement formation for engagement with one or more latching members of the transducer unit. The engagement formation may be part of the casing of the container. For example, the engagement formation may be an engagement collar of the casing, and may be defined, in part, by an annular channel in the casing. The latching members of the transducer unit may comprise clip formations for engagement with the channel. In another example, the engagement means comprises one or more latching members for engagement with an engagement formation of the transducer unit. For example, the latching members may comprise engagement arms arranged to cooperate with a collar of the transducer unit.

The container may be releasably attachable to the transducer unit. In this way, the transducer unit may be re-usable and the container may be disposable after use. Alternatively, the container may be permanently attachable to the transducer unit, for example when the transducer unit is also disposable, or when the container is re-usable. In that context, the present invention extends to a container that forms an integral part of or is permanently attached to a transducer unit.

The container may be suitable for use with a transducer unit comprising a plurality of transducers. In such an arrangement, the transducers may be operable individually or simultaneously. By providing multiple transducers in an array, the size and height of the transducer unit can reduced compared with a transducer unit with equivalent performance that uses only one transducer element.

The container may therefore comprise a corresponding plurality of chambers, each chamber having a respective contact surface arranged to contact a respective output face of an associated one of the plurality of transducers.

The contact medium used with the container is preferably a water-based ultrasound gel, such as is known in the art. For example, the contact medium may include viscosity modifiers such as propylene glycol or glycerine. The contact medium may also include cavitation enhancers. The medicament may be incorporated into the contact medium in any suitable way to preserve the character of the medicament. For example, the medicament may form a solution, suspension, colloid, sol, emulsion or other dispersion in the contact medium.

From a second aspect of the invention, there is provided a transducer unit for transdermal delivery of a medicament. The transducer unit comprises at least one transducer having an output face and is arranged for attachment to a container according to the first aspect of the invention.

Preferably, the transducer unit is a self-contained device for medicament delivery that can be re-used, with a fresh container according to the first aspect of the invention being provided for each use. To this end, the transducer unit may include a control circuit for the transducer, such as a signal generator, and/or a power supply for the transducer, such as a battery.

The output face of the transducer may be planar. Advantageously, when used with a container having a convex contact surface, the planar output face progressively flattens the contact surface to exclude air from the interface between the contact surface and the output face. The transducer may be arranged for partial insertion into the container when the container is attached to the transducer unit. For example, the transducer unit may include a recess around the transducer for accepting a part of the container, such as a collar of the container.

The transducer unit may comprise a socket for accepting the container. The socket may comprise a guide region for guiding the container into the socket.

The transducer unit may include latching means for engagement with a corresponding engagement formation of the container. Similarly, the transducer unit may include an engagement formation for cooperation with corresponding latching means of the container.

The transducer unit may comprise release means for cooperation with a latching member of the transducer unit or the container to release the container from the transducer unit. For example, the release means may comprise a button or another suitable user-activated device.

The invention also extends to a transducer unit according the second aspect of the invention in combination with a container according to the first aspect of the invention. In particular, the invention may be embodied as a medicament delivery device comprising such a combination.

A further aspect of the invention provides a medicament delivery device for transdermal delivery of a medicament through a patient's skin, comprising a transducer unit having a transducer with an output face, an operating chamber for receiving a coupling medium, a reservoir for storing the coupling medium before use of the device, and transfer means operable to transfer the coupling medium from the reservoir to the operating chamber thereby to form an acoustic coupling between the output face of the transducer and the coupling medium.

In this way, the coupling medium can be contained within the reservoir until the device is ready for use, thereby preserving the sterility of the coupling medium. When preparing the device for use, the transfer means can be operated to transfer the coupling medium to the operating chamber. For example, the device may be placed against the user's skin, and then the transfer means can be operated to fill the space between the output face of the transducer and the patient's skin with the coupling medium. Such an arrangement can be particularly useful when the coupling medium has a low viscosity.

The device may comprise a container for housing the operating chamber. The container may be attached or attachable to the transducer unit. The reservoir may be external to the container. Alternatively, the container may house the reservoir. For example, the container may comprise a chamber divided into an operating chamber and a reservoir portion. The transfer means may comprise a piston, a deformable wall or any other suitable means. The acoustic coupling between the output face and the coupling medium may be through direct contact between the coupling medium and the output face. Alternatively, the acoustic coupling may be indirect, such as through a contact membrane disposed between the output face and the coupling medium.

In another aspect of the present invention, there is provided a container for containing a coupling medium for transdermal delivery of a medicament using a transducer unit having a transducer with an output face. The container comprises a contact surface for contacting the output face of the transducer to provide acoustic coupling between the output face of the transducer and the coupling medium, and a chamber for receiving the coupling medium. The container is attachable to the transducer unit and is arranged such that, upon attachment of the container to the transducer unit, a coupling is formed between the output face of the transducer and the contact surface. Preferably, the coupling is substantially ultrasonically transparent. Said another way, a coupling is formed that does not substantially attenuate or reduce ultrasonic transmission across the coupling.

Preferred and/or optional features of each aspect of the invention may be used, alone or in appropriate combination, in the other aspects of the invention also.

FIG. 1, which has already been referred to above, is a schematic illustration of medicament delivery using sonophoresis. Embodiments of the present invention will now be described, by way of example only, with reference to the remaining accompanying drawings, in which like reference numerals are used for like features, and in which:

Figure 2:
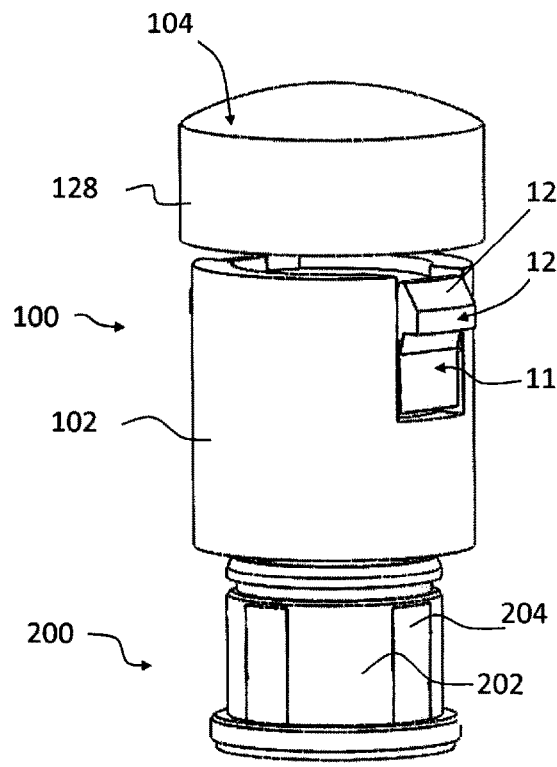
FIG. 2 is an isometric view of a medicament delivery apparatus comprising a transducer unit and a first container.
Figure 3:
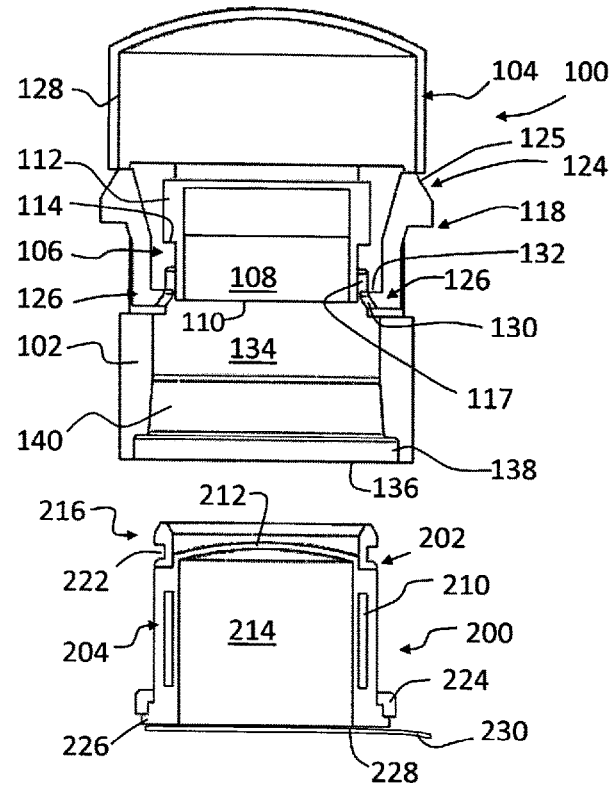
FIG. 3 is a cross-sectional view of the apparatus of FIG. 2.
Figure 4:
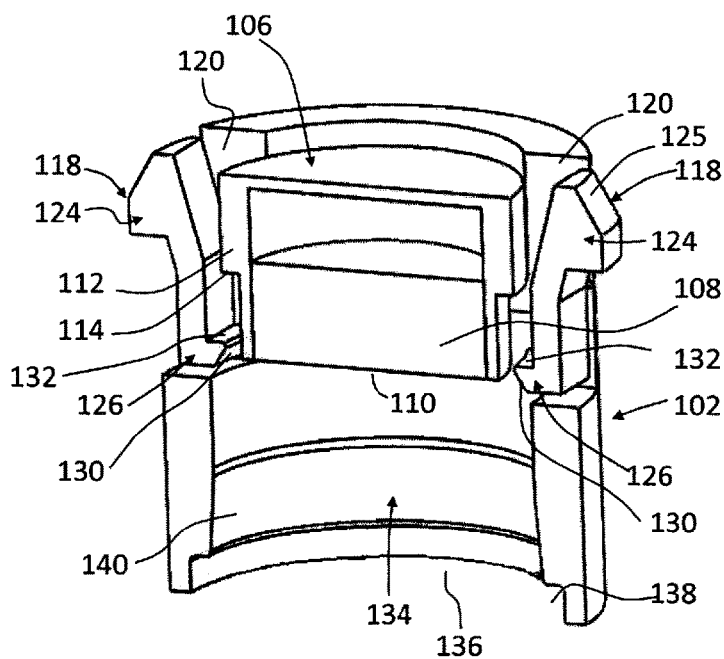
FIG. 4 is a part-sectional isometric view of part of the transducer unit of the apparatus of FIG. 2.
Figure 5:
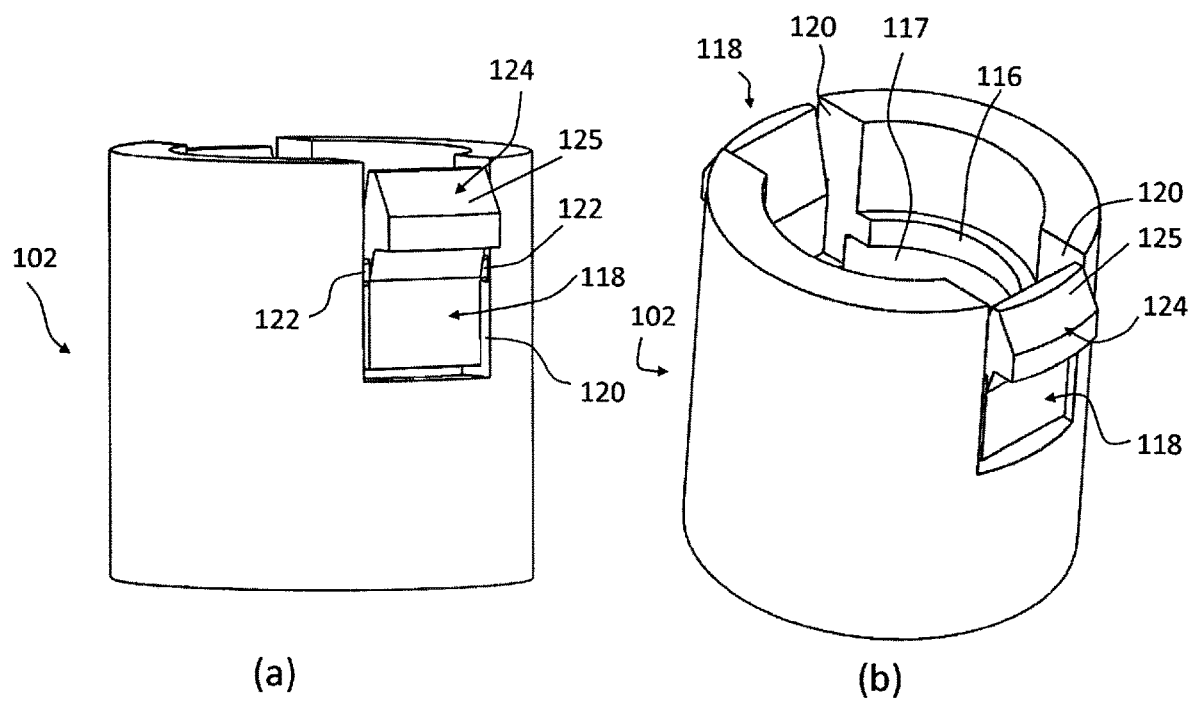
Figure 9:
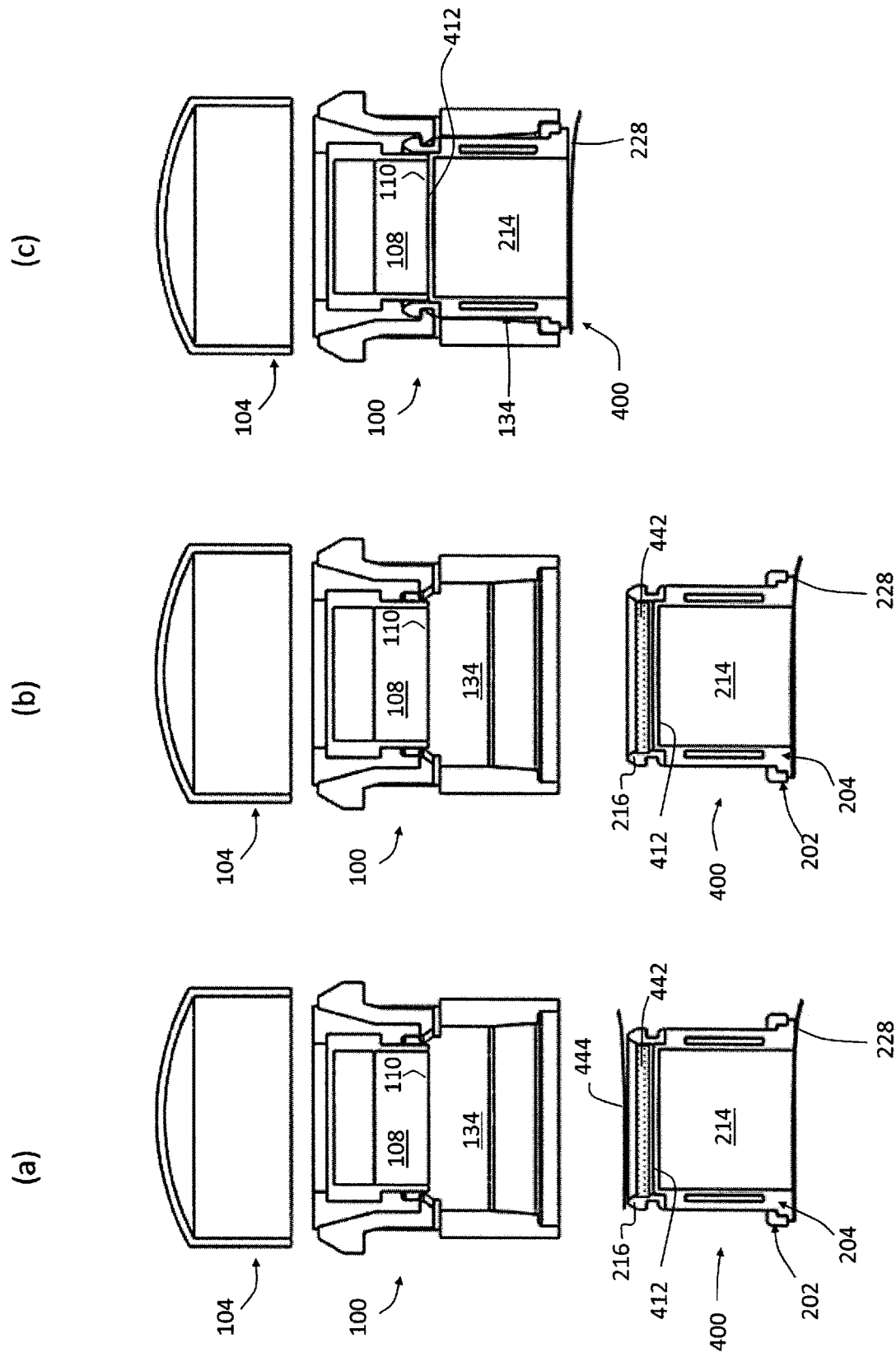
Figure 10:
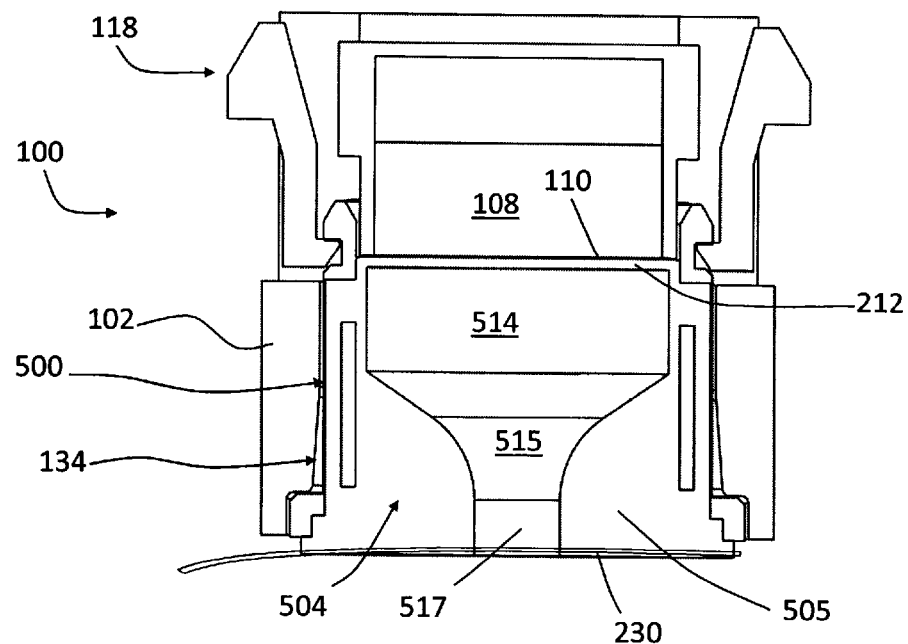
Figure 11:
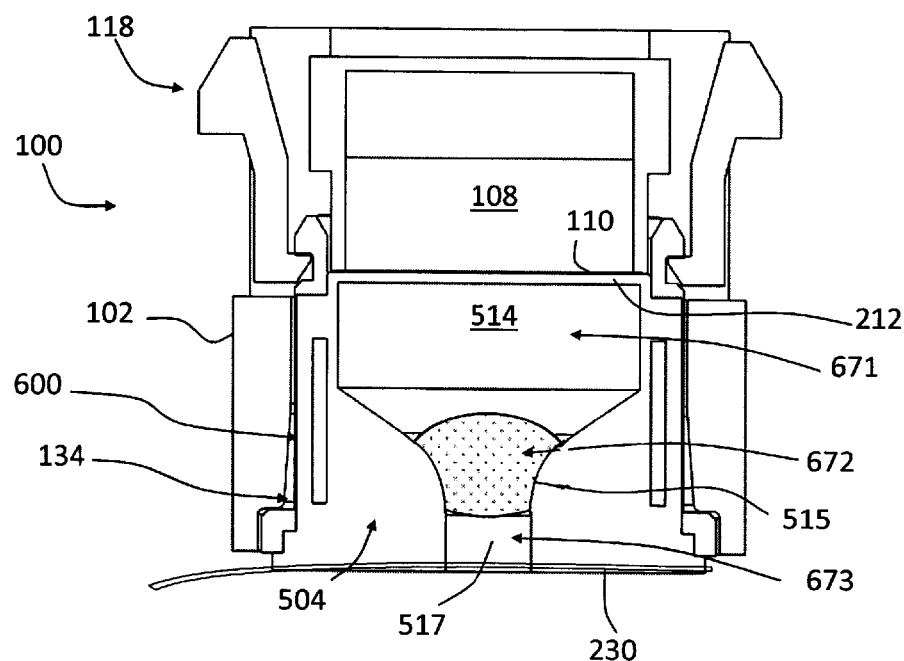
Figure 12:
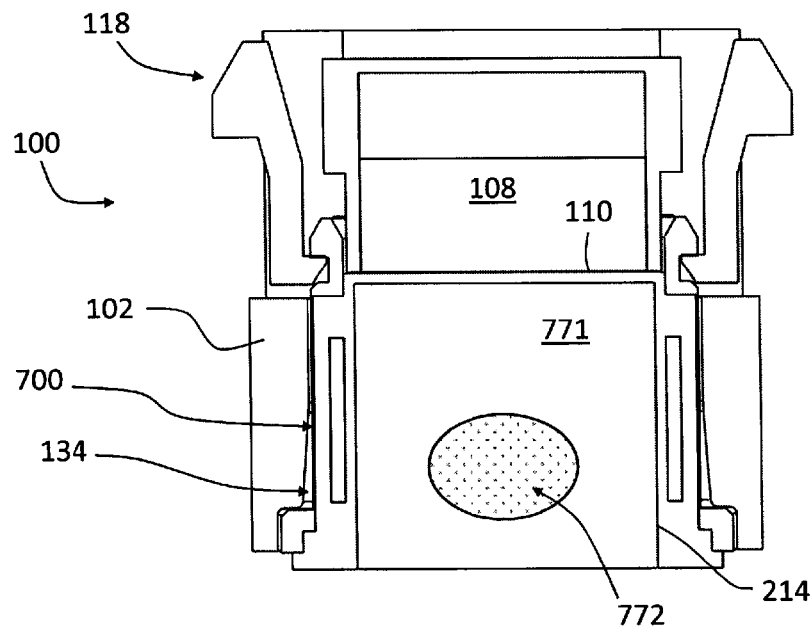
Figure 13:
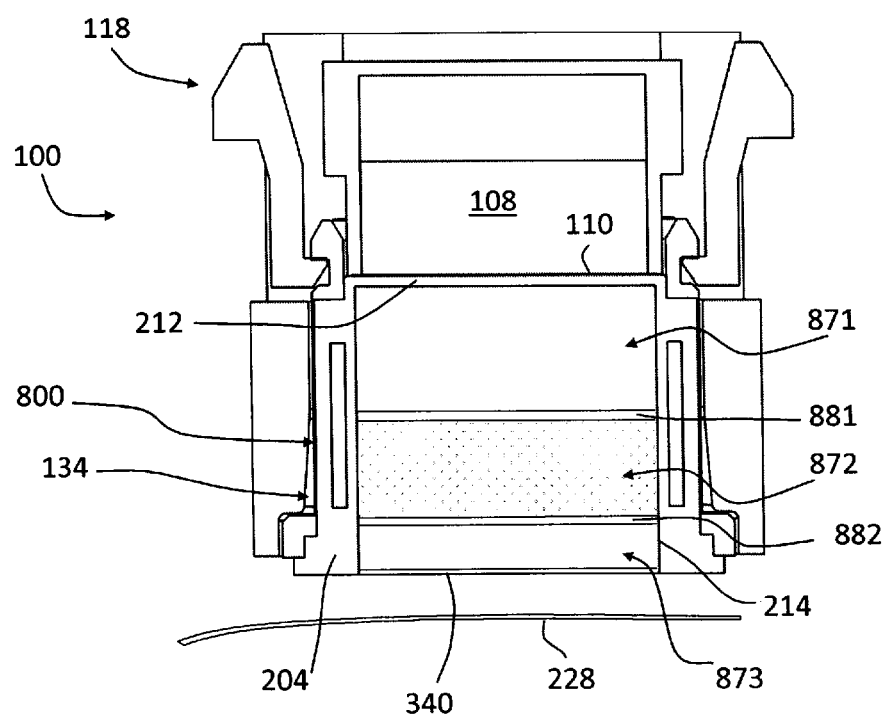
Figure 14:
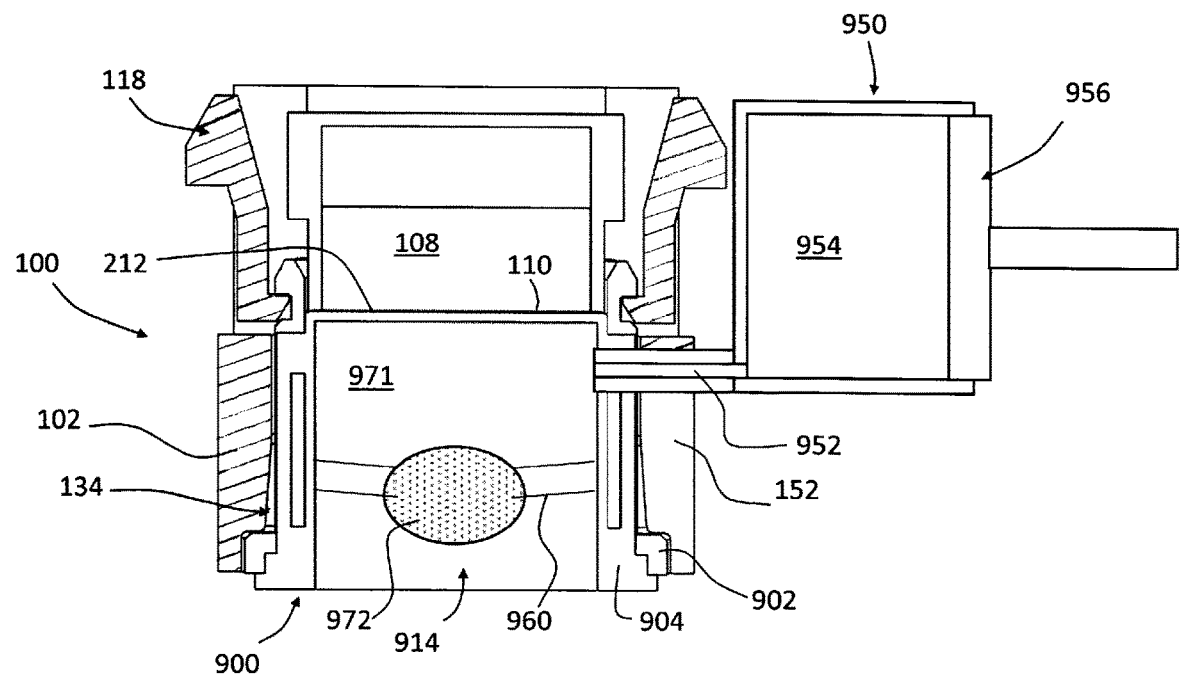
Figure 15:
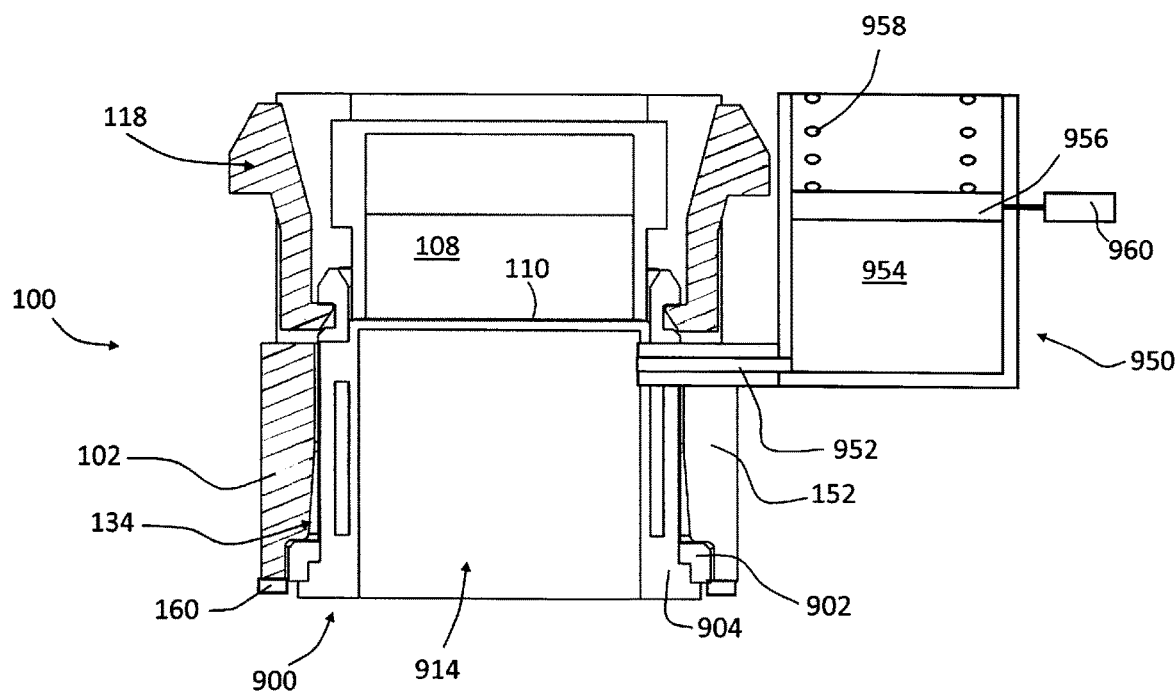
Figure 18:
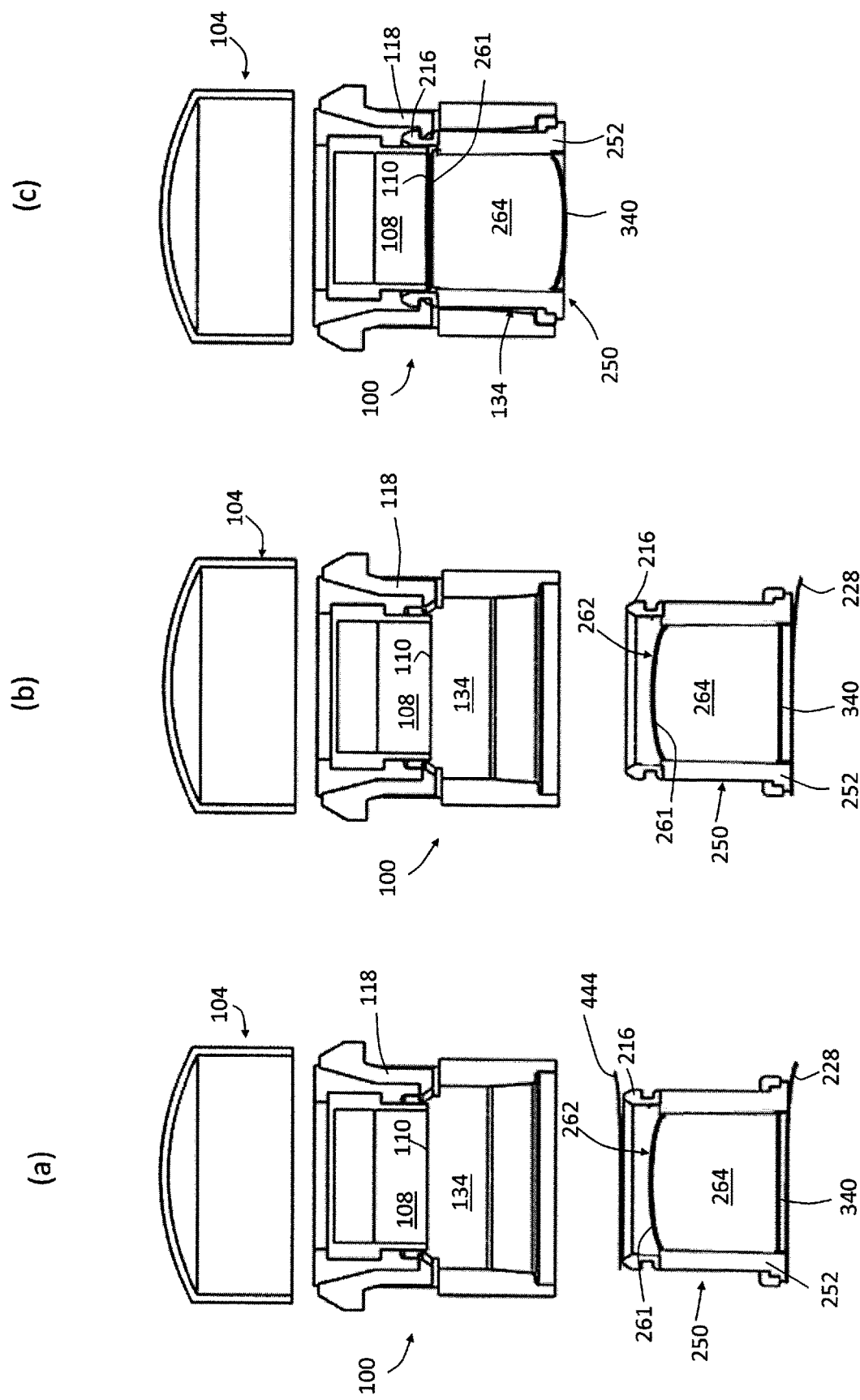
Figure 19:
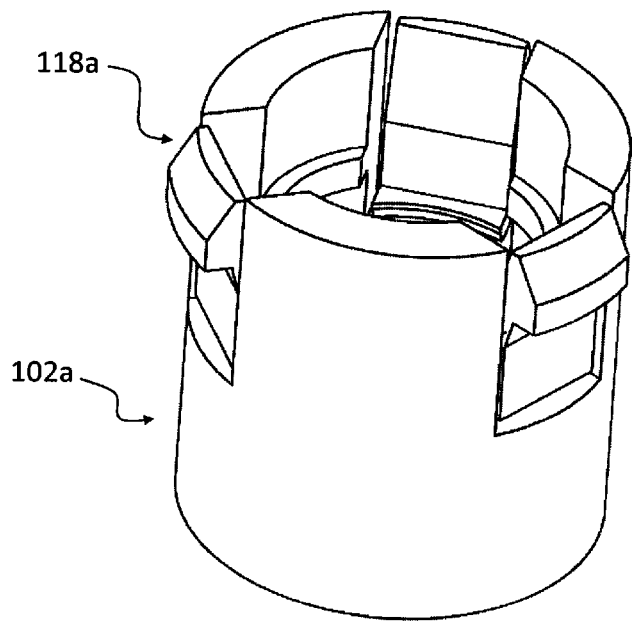
Figure 20:
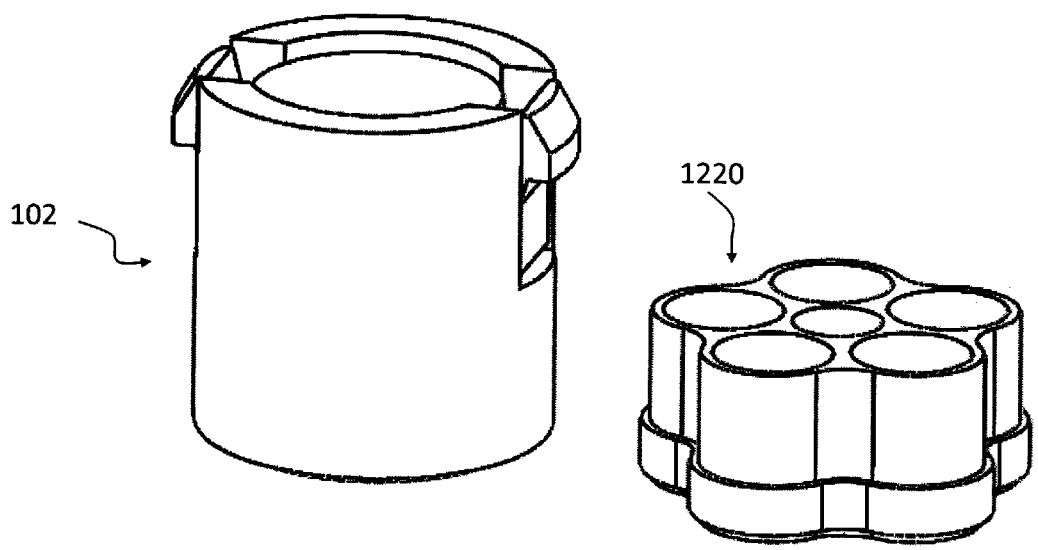

FIGS. 5(a) and 5(b) are isometric views of a housing part of the transducer unit of FIG. 4;

FIGS. 6(a) and 6(b) are part-sectional isometric views of a casing part of the container and an assembled container of the apparatus of FIG. 2, respectively;

FIGS. 7(a) to 7(c) are cross-sectional views illustrating a sequence of steps in the use of the apparatus of FIG. 2;

FIGS. 8(a) to 8(c) are cross-sectional views illustrating a sequence of steps in the use of the transducer unit of FIG. 3 with a second container;

FIGS. 9(a) to 9(c) are cross-sectional views illustrating a sequence of steps in the use of the transducer unit of FIG. 3 with a third container;

FIG. 10 is a cross-sectional view of the transducer unit of FIG. 3 in use with a fourth container;

FIG. 11 is a cross-sectional view of the transducer unit of FIG. 3 in use with a fifth container;

FIG. 12 is a cross-sectional view of the transducer unit of FIG. 3 in use with a sixth container;

FIG. 13 is a cross-sectional view of the transducer unit of FIG. 3 in use with a seventh container;

FIG. 14 is a cross-sectional view of a modified transducer unit in use with an eighth container;

FIG. 15 is a cross-sectional view of another modified transducer unit in use with a variant of the eighth container;

FIGS. 16(a) and 16(b) are cross-sectional views illustrating a sequence of steps in use of a transducer unit and a ninth container;

FIGS. 17(a) and 17(b) are cross-sectional views illustrating a sequence of steps in use of a transducer unit and a tenth container;

FIGS. 18(a) to 18(c) are cross-sectional views illustrating a sequence of steps in the use of the transducer unit of FIG. 3 with an eleventh container;

FIG. 19 is an isometric view of a variant of the housing part of the transducer unit of FIG. 3;

FIG. 20 is an isometric view of the transducer unit of FIG. 3 alongside an alternative transducer unit; and FIGS. 21(a) to 21(c) are part-sectional isometric views showing a sequence of steps in the use of the alternative transducer unit of FIG. 20 with a corresponding container.

A medicament delivery device in accordance with one embodiment of the present invention is shown in FIGS. 2 and 3. The apparatus of the device includes a transducer unit 100, and a container 200 arranged to engage releasably with the transducer unit 100. The container 200 is designed to hold a coupling medium in contact with a patient's skin during use of the device. Throughout the following description, the term "distal" and related terms are used to refer to the end of the apparatus that is towards the patient's skin in use (i.e. the lower end in FIGS. 2 and 3), and the term "proximal" and related terms are used to refer to the end of the apparatus that is furthest from the skin in use (i.e. the upper end in FIGS. 2 and 3). In FIGS. 2 and 3, the container 200 is shown disengaged from the transducer unit 100.

The transducer unit 100 is a hand-held device with a generally cylindrical, elongate form, and comprises a generally tubular housing 102 and a cap-shaped release button 104 disposed at a proximal end of the housing 102. An opposite, distal end of the housing is open to receive the container 200 in use. FIG. 4 shows the transducer unit 100 with the release button 104 omitted for clarity, and FIGS. 5(a) and 5(b) show the housing 102 of the transducer unit in isolation from the other components.

A transducer module 106, visible in FIGS. 3 and 4, is received in the housing 102. The transducer module 106 includes an ultrasonic transducer element 108 having an output face 110 which is exposed on the distal side of the transducer module 106. The transducer element 108 may be piezoelectric, capacitive or any other suitable type.

The transducer element 108 is retained in a cup-shaped casing 112. The outer wall of the casing 112 includes a step 114 that locates against a collar 116 in the inner wall of the housing 102 (shown most clearly in FIG. 5(b)). The casing 112 may be attached to the housing 102 by mechanical engagement, adhesive or other suitable means. A signal cable (not shown) is used to connect the transducer element 108 to an ultrasonic signal generator (not shown), which is preferably battery-powered and housed in the transducer unit 100.

An annular recess 117 is defined between the outer wall of the casing 112 and the inner wall of the housing 102, on a distal side of the collar 116. As will be explained in more detail below, the recess 117 accepts a collar part of the container 200 when the container 200 is attached to the transducer unit 100.

A pair of latching members 118 are disposed on diametrically opposite sides of the housing 102. Each latching member 118 is accommodated in a respective slot 120 in the wall of the housing 102. Each latching member 118 is attached to the housing 102 by a pair of connecting members 122 (most clearly seen in FIG. 5(a)) that extend circumferentially from each side of the latching member 118 to connect with the walls of the respective slot 118. The connecting members 122 are flexible to allow the latching members 118 to pivot about a neutral position under the application of an external force, causing the connecting members 122 to twist, but are resilient to return the latching members 118 to the neutral position when no force is applied.

In this example, the latching members 118, connecting members 122 and housing 102 are moulded as a single component, but it will be appreciated that the housing 102, the latching members 118 and/or the connecting members 122 could be formed as two or more separate components. The latching members 118 could be biased to return to the neutral position by any suitable means, such as by springs or other biasing means.

Each latching member 118 includes a head portion 124, disposed proximally with respect to the connecting members 122, and a clip formation 126 disposed distally with respect to the connecting members 122. Each of the head formations 124 projects radially outside the cylindrical outer wall of the housing 102 and includes a ramped proximal face 125 that cooperates with a tubular skirt 128 of the release button 104. Each of the clip formations 126 has a ramped distal side 130 and a proximal side 132 that is generally perpendicular to the axis of the tubular housing 102. As best seen in FIG. 3, the proximal side 132 of each clip formation 126 is located proximally with respect to the output face 110 of the transducer element 108, adjacent to the recess 117.

Referring now to FIGS. 2, 3, 6(a) and 6(b), the container 200 comprises a generally tubular casing 202 and a liner 204. The liner 204 covers the inner wall of the casing 202 and is formed from a flexible elastomeric material with low acoustic attenuation, such as silicone rubber.

The casing 202, which is shown without the liner in FIG. 6(a), is preferably formed from a rigid plastics material. The casing is provided with a plurality of longitudinally-extending recesses 206 in its outer face. At each end of each recess, an aperture 208 is formed through the wall of the casing 202. In the illustrated example, the casing 202 includes four recesses 206 and eight apertures 208, although it will be appreciated that fewer or more apertures and recesses could be present.

During manufacture of the container 200, the liner 204 is moulded or cast over the casing 202 so that the material of the liner 204 fills the apertures 208 and the recesses 206. In this way, bridging portions 210 of the casing 202 are embedded in the liner 204 to attach the liner 204 to the casing 202.

At its proximal end, the liner 204 extends across the interior of the casing 202 to form a coupling membrane or contact membrane 212. In this way, the liner 204 defines a generally cylindrical chamber 214 which is open only on its distal side and which is separated from the casing 202 by the liner. The contact membrane 212 therefore defines, in part, the chamber 214.

An engagement formation in the form of a collar 216 of the casing 202 is disposed on the proximal side of the contact membrane 212. The proximal end of the engagement collar 216 has bevelled inner and outer surfaces 218, 220. An annular channel 222 extends circumferentially around the outer wall of the casing 202 to define the distal side of the engagement collar 216.

The distal end of the casing 202 is stepped outwardly to define an enlarged-diameter skirt portion 224. As shown in FIGS. 3 and 6(b), the distal end of the liner 204 is formed into an annular foot 226 that partially covers the distal end of the skirt portion 224.

Referring again to FIGS. 3 and 4, a distal portion of the housing 102 provides a socket 134 for receiving the container 200. The socket 134 is accessed by an aperture 136 in the distal end face of the housing 102. An annular recess 138 is formed at the end of the inner wall of the housing 102 around the periphery of the aperture 136. Adjacent to the recess 138, the inner wall is frustoconically shaped to define a guide region 140 of the socket 134, in which the diameter of the socket 134 widens towards the aperture 138.

The function of the container 200 is to hold a medicament-loaded coupling medium in place in the chamber 214 between the output face 110 of the transducer element 108 and a user's skin for sonophoresis. The transducer unit 100 is intended to be a re-usable part, whilst the container 200 is a single-use component that can be discarded after use. In this embodiment, the container 200 is intended to be pre-filled with the coupling medium for supply to a user. To retain the coupling medium in the chamber 214 of the container 200 during storage, handling and transport, and to maintain its sterility before use, an peelable sealing film 228 is affixed to the distal side of the foot 226 of the liner 204, for example by a suitable adhesive.

The coupling medium may be of a type generally known in the art as an ultrasound gel or coupling agent. Preferably, the coupling medium is water-based.

For effective sonophoresis, it is desirable to maximise ultrasonic intensity in the coupling medium. Accordingly, it is important to ensure that the ultrasonic waves can propagate from the output face 110 of the transducer element 108 across the contact membrane 212 and into the coupling medium in the chamber 214 with minimum attenuation or alteration by the contact membrane itself or at its interfaces. The material of the contact membrane 212 and the liner 204 is therefore preferably impedance-matched with the coupling medium. For example, the material of the contact membrane 212 and the liner 204 may be a silicone rubber material.

It is also important that, when the container 200 is fitted to the transducer unit 100, the contact membrane 212 is brought into intimate contact with the output face 110 of the transducer element without air becoming entrapped at the interface.

As will now be explained, to help facilitate good acoustic coupling between the transducer element output face 110 and the membrane 212, the process of attaching the container 200 to the transducer unit 100 causes the formation of a substantially air-free coupling between the membrane 212 and the transducer output face 110.

In this embodiment of the invention, the contact membrane 212 is dome-shaped so that it bulges in the proximal direction when the chamber 214 is filled with the coupling medium. In this way, the contact membrane 212 presents a convex coupling surface at the proximal end of the container 200.

When the container 200 is pushed into the socket 134 (as will be described in more detail below), contact between the output face 110 and the membrane 212 first occurs at the central point of the membrane 212 (i.e. at the apex of the dome). The area of contact then progressively increases in size as it spreads outwards to the periphery of the membrane 212 as the output face 110 flattens the dome, expelling air and avoiding any entrapment of air at the interface between the output face 110 and the membrane 212.

A sequence of steps in the use of the apparatus will now be described with reference to FIGS. 7(a) to (c).

First, the container 200 is inserted into the socket 134 of the transducer unit 100, through the aperture 136. The guide portion 140 of the socket 134 helps to align the axes of the container and the transducer unit 100. As shown in FIG. 7(a), the bevelled outer surface 220 of the engagement collar 216 slides over the ramped distal side 130 of the clip formation 126 on each of the latching members 118, forcing the latching members 118 to pivot with respect to the housing 102 and the connecting members 122 to twist. The apex of the contact membrane 212 contacts the output face 110 of the transducer element 108 as the engagement collar 216 begins to cooperate with the latching members 118.

As the container 200 is pushed further into the socket, the clip formations 126 of the latching members 118 ride over the engagement collar 216 and then snap into the channel 222 as the connecting members 122 untwist to return the latching members 118 to their original, neutral positions. As shown in FIG. 7(b), the proximal sides 134 of the clip formations 126 engage with the distal side of the engagement collar 216 to lock the container 200 in the socket 134, with the engagement collar 216 in the recess 117 that surrounds the output face 110 of the transducer element 108.

When in this locked position, the contact membrane 212 lies flat against the output face 110 of the transducer element 108. Because contact between the initially-domed contact membrane 212 and the output face 110 occurs progressively as described above, good acoustic coupling between the output face 110 and the contact membrane 212 is achieved. Furthermore, the latching members 118 are arranged to engage with the engagement collar 216 only once the contact membrane 212 has been pressed flat against the output face 110 of the transducer element 108, so as to deter use of the device before acoustic coupling between the output face 110 and the contact membrane 212 has been achieved.

As can also be seen in FIG. 7(b), when the container 200 is in the locked position, the skirt portion 224 of the container casing 202 is accommodated in the recess 138, leaving part of the foot portion 226 of the liner 204 protruding on the distal face of the housing 102.

To prepare the apparatus for operation, the sealing film 228 is removed to expose the coupling medium in the chamber 214. The distal end of the apparatus is then placed against the skin (not shown) to bring the coupling medium into contact with the skin. Because the material of the liner 204 is flexible, the foot portion 226 of the liner 204 can conform to the skin, creating a barrier to guard against leakage of the coupling medium.

A small volume of coupling medium will be displaced when the container 200 is inserted into the transducer unit 100, as the domed contact membrane 212 is flattened by the output face 110 of the transducer element 108. Initially, the displaced volume can be accommodated by distortion of the sealing film 228. After removal of the film, the displaced volume helps to avoid air entrapment as contact between the coupling medium and the skin is established.

In this way, the container 200 holds the coupling medium in contact with the skin and in acoustic contact with the output face 110 of the transducer element 108. By application of a suitable signal to the transducer element 108, the medicament in the coupling medium can be transported through the skin by sonophoresis.

After a pre-determined treatment time, during which a dose of medicament is delivered, the apparatus can be removed from the skin. It is then necessary to remove the used container 200 from the transducer unit 100 for disposal. As shown in FIG. 7(c), to release the container 200, the release button 104 is moved distally with respect to the housing 102 of the transducer unit 100. The tubular skirt 128 of the release button 104 bears against the ramped proximal face 125 of the head 124 of each of the latching members 118. This causes the latching members 118 to pivot so that the clip formations 126 move out of the channel 222, allowing the container 200 to separate from the transducer unit 100.

It will be appreciated that the contact membrane 212 may act to apply a force to the output face 110 of the transducer element 108 that encourages separation of the container 200 from the transducer unit 100 once the latching members 118 have been released. For instance, when the container 200 is first attached to the transducer unit 100, the contact membrane 212 may elastically deform as it conforms to the output face 110 of the transducer element 108. This resulting in a corresponding elastic reaction force on the output face 110 that biases the container 200 away from the output face 110 once the container 200 is unlatched.

In the above-described embodiment, the liner 204 of the container is moulded so that the contact membrane 212 is dome-shaped, even when the chamber 214 is empty. However, it will be appreciated that the contact membrane 212 could be planar when the chamber 214 is empty, and that the dome shape could be formed by overfilling the chamber 214 with coupling medium so that the membrane 212 bulges in the proximal direction.

Although not shown, a sealing film could also be used to seal the proximal end of the container 200 before use to prevent contamination of the contact membrane 212. For example, a sealing film could be affixed to the proximal end face of the engagement collar 216 by a suitable adhesive, and the sealing film could be peeled away and discarded before insertion of the container 200 into the transducer unit 100.

Various modifications in the design of the container are possible, as will now be described.

FIGS. 8(a) to 8(c) show the transducer unit 100 in use with a second container 300. The second container 300 is generally similar to the first container 200 and only the differences will be described in detail. For simplicity, the release button of the transducer unit is not shown in FIGS. 8(a) to 8(c).

The second container 300 includes a closure membrane 340 that extends across the distal end of the chamber 214. The closure membrane 340 serves to contain the coupling medium in the chamber 214 after the sealing film 228 is removed. Accordingly, the second container 300 is particularly useful when the coupling medium is of low viscosity.

The closure membrane 340 is formed from a material through which the coupling medium can penetrate only during sonophoresis. Preferably, therefore, the closure membrane 340 behaves in a similar manner to skin, which is normally impermeable but which can be penetrated by microjets formed during sonophoresis. The closure membrane 340 may be formed from a skin substitute material. The closure membrane 340 is attached to the foot portion 226 of the liner 204, for example by means of a suitable adhesive.

FIG. 8(a) shows the apparatus when the second container 300 has been located in the socket 134 of the transducer unit 100 but has not yet been engaged with the latch members 118. Initially, with the chamber 214 filled with coupling medium, the closure membrane 340 has a domed shape, similar to the domed shape of the contact membrane 212, but with a larger radius of curvature (i.e. a less pronounced dome). Accordingly, the closure membrane 340 provides a concave surface at the distal end of the container 300. As with the first container 200, the distal end of the second container 300 is sealed with a sealing film 228, which in this case maintains the sterility of the closure membrane 340 until the container is ready for use.

As the container 300 is inserted further into the socket 134, the output face 110 of the transducer element 108 comes into contact with the contact membrane 212, causing the domed shape of the contact membrane 212 to flatten progressively. FIG. 8(b) shows an intermediate stage during insertion, in which the engagement collar 216 of the container 300 is displacing the latching members 118. As the contact membrane 212 flattens, the coupling medium in the chamber 214 is displaced to cause flattening of the closure membrane 340. The sealing film 228 is not shown in FIG. 8(b) for clarity, but it would preferably be left in place until the container 300 is fully engaged with the transducer unit 100.

FIG. 8(c) shows the container 300 engaged with the transducer unit 100, with the collar 216 in the recess 117, the clip formations 126 of the latching members 118 in engagement with the channel 222 of the container 300, and the contact membrane 212 flat against the output face 110 of the transducer element 108. The closure membrane 340 is now domed in the distal direction to present a convex surface at the distal end of the container 300.

After removal of the sealing film 228, the closure membrane 340 can be placed against the skin. The domed shape of closure membrane 340 assists in achieving good contact between the closure membrane 340 and the skin.

In a variant (not shown) of the second container, the closure membrane is initially flat, and bulges into a convex shape upon attachment of the container to the transducer unit. In a further variant, the closure membrane is initially dome-shaped and has the same radius of curvature as the initial domed shape of the contact membrane. Accordingly, in this variant, when the closure membrane is pushed flat against the output face of the transducer element, the closure membrane presents a flat surface at the distal end of the container.

The first and second containers 200, 300 described above achieve good acoustic coupling between the contact membrane 212 and the output face 110 of the transducer element 108 by virtue of the initial domed shape of the contact membrane 212, which comes into contact progressively with the planar output face 110, thereby avoiding entrapment of air at the interface. It will be appreciated that same result could be achieved with a different initial convex shape of the contact membrane, such as a conical or pyramidal shape. The contact membrane could also be inclined at an angle to the output face so that contact occurs first at one side of the membrane and then progresses across the membrane as the container and the transducer unit come into contact. It is also conceivable that the output face of the transducer element could be suitably shaped to assist in the exclusion of air from the interface. For instance, the output face could be conical or inclined.

FIGS. 9(a) to 9(c) shows the transducer unit 100 in use with a third container 400, in which another alternative way of achieving good acoustic contact between the transducer element and the coupling medium is employed. The third container 400 is generally similar to the first container 200 and only the differences will be described in detail.

In the third container 400, the contact membrane 412 is planar, rather than domed. A contact medium comprising an ultrasonic coupling medium is applied to the proximal side of the contact membrane 412 to form a contact layer 442. A sealing film 444 is affixed to the engagement collar 216 at the proximal end of the container 400 to seal the coupling medium of the contact layer 442 in the container 400. The coupling medium of the contact layer 442 is preferably the same as the coupling medium used in the chamber 214, but no medicament is present in the contact layer 442.

FIG. 9(a) shows the container 400 and the transducer unit 100 in an initial state. The container 400 is sealed at both ends by the respective sealing films 444, 228. The sealing film 444 at the proximal end is then removed to expose the contact layer 442, as shown in FIG. 9(b).

The container 400 is then inserted into the socket 134 of the transducer unit 100, so as to press the contact layer 442 against the output face 110 of the transducer element 108. In this way, the coupling medium in the contact layer 442 helps to ensure good acoustic coupling between the output face 110 of the transducer element 108 and the contact membrane 412. Once the container 400 is fully engaged with the transducer unit 100, as shown in FIG. 9(c), some or all of the coupling medium of the contact layer 442 may be displaced away from the interface between the output face 110 and the contact membrane 412. After engagement of the container 400 with the transducer unit 100, the sealing film 228 on the distal end of the container 400 can be removed before application of the device to the skin.

In a variant of the third container, a closure membrane of the type used in the second container 300 is also provided to close the coupling medium chamber.

Although not illustrated, other ways of forming a substantially air-free coupling between the contact membrane of the container and the output face of the transducer element are possible. For example, suitable cooperating elements of the container and the transducer unit could be provided to create a vacuum between the contact membrane and the output face of the transducer unit as the container is brought into engagement with the transducer unit.

Figure 1:
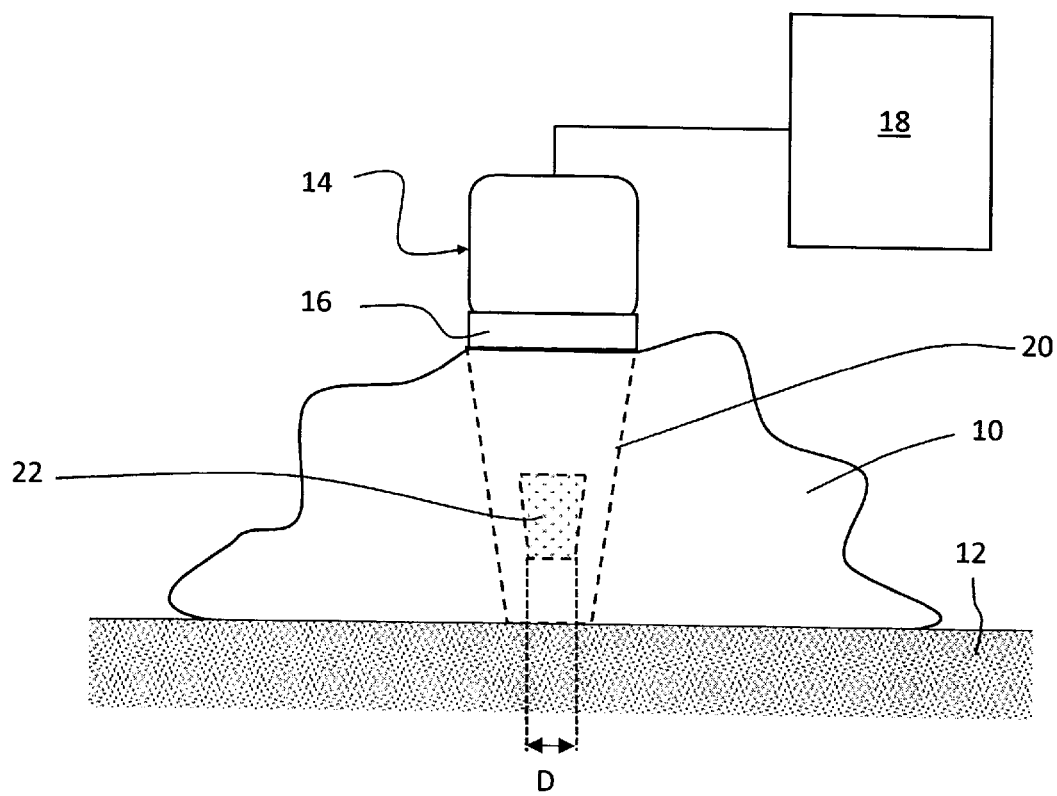

As described above with reference to FIG. 1, during sonophoresis, ultrasound-induced cavitation occurs predominantly in a relatively small volume of the coupling medium corresponding to the focusing zone of the ultrasonic vibrations. Accordingly, medicament that is dispersed in the coupling medium that lies outside the focusing zone is unlikely to be transported through the skin during sonophoresis and would therefore be discarded along with the container after use. As a result, a relatively high wastage of medicament can occur.

FIG. 10 shows the transducer unit 100 in use with a fourth container 500 that is designed to reduce medicament wastage. The fourth container 500 is generally similar to the first container 200 already described above, and only the differences will be described in detail.

In the fourth container 500, the chamber 514 that receives the coupling medium is shaped so that the chamber 514 does not extend to regions which are not expected to be exposed to ultrasonic excitation during sonophoresis. In particular, a distal part 505 of the liner 504 of the fourth container 500 is shaped with an increasing wall thickness moving towards the distal end of the container 500, such that a distal part 515 of the chamber 514 is generally funnel-shaped. The chamber 514 terminates at its most distal end at a circular aperture 517 with a reduced diameter compared with the chambers of the first, second and third containers 200, 300, 400, but with a diameter that is larger than the diameter of the treatment area (D in FIG. 1).

In this way, the volume of the chamber 514 of the fourth container 500 is reduced compared with the volume of the chamber 214 of the first, second and third containers 200, 300, 400. The amount of medicament-loaded coupling medium required to fill the chamber 514 of the fourth container 500 is correspondingly reduced, without substantially affecting the amount of medicament that can be delivered from the container 500 during sonophoresis. It will be understood that the shape of the chamber 514, and in particular the funnel-shaped region 515, can be modified as appropriate for the particular characteristics of ultrasound transmission from a given transducer element, coupling medium and apparatus geometry.

In a variant of the fourth container (not shown), the liner has a substantially uniform thickness, and instead the casing is shaped to define a funnel-shaped region of the chamber.

In the container shown in FIG. 10, medicament is dispersed uniformly throughout the coupling medium in the chamber 514. As a consequence, a relatively large amount of medicament is still wasted. For example, medicament in the coupling medium outside the funnel-shaped region 515 of the chamber 514 is unlikely to be transported through the skin during sonophoresis. To further reduce medicament wastage, in further embodiments of the invention, medicament is dispersed non-uniformly in the coupling medium, as will now be described.

FIG. 11 shows the transducer unit 100 in use with a fifth container 600. The fifth container 600 is identical to the fourth container 500 described above with reference to FIG. 10, except in that the chamber 514 is filled with three layers of coupling medium.

A first layer 671 comprising a medicament-free coupling medium is disposed at the proximal end of the chamber 514, adjacent to the contact membrane 212. A second layer 672, comprising a medicament-loaded coupling medium, is disposed adjacent to the first layer 671 and within the funnel-shaped region 515 of the chamber 514. A third layer 673, again comprising a medicament-free coupling medium, is disposed adjacent to the second layer 672 and extends to the aperture 517 at the distal end of the container 600.

The position of the second layer 672 corresponds approximately to the focusing zone of the transducer element 108, and is therefore the predominant source of material for transportation through the skin during sonophoresis. The first layer 671 and the third layer 673 primarily serve to facilitate acoustic transmission from the output face 110 of the transducer element 108 to the second layer 672 and from the second layer 672 to the skin, respectively. Because only the second layer 672 contains medicament, wastage of medicament is substantially reduced.

In some variants, the third layer 673 may be self-supporting. For example, the third layer 673 may comprise a coupling medium with relatively high viscosity compared with the second layer 672. In this way, the third layer 673 can act as a barrier to prevent leakage of the medicament-loaded coupling medium in the second layer 672 through the aperture 517, such that no closure membrane is required. The first layer 671 may also comprise a coupling medium with relatively high viscosity compared with the second layer 672, to reduce diffusion of medicament out of the second layer 672.

FIG. 12 shows the transducer unit 100 in use with a sixth container 700. The sixth container 700 is identical to the first container 200, except in that the medicament is non-uniformly distributed in the chamber 214 of the sixth container 700.

In this case, a support portion 771 of the chamber 214 is filled with a medicament-free coupling medium with relatively high viscosity. A medicament-containing volume 772 of medicament-loaded coupling medium, with relatively low viscosity, is suspended in the support portion 771. The support portion 771 therefore fills the chamber 214 around the medicament-containing volume 772 and keeps the medicament-containing volume 772 in position within the chamber 214. The medicament-containing volume 772 is positioned to correspond with the focusing zone of the acoustic vibrations. In this way, the sixth container 700 utilises the simple cylindrical chamber geometry of the first to third containers whilst reducing medicament wastage.

The sixth container 700 can be manufactured by first filling the chamber 214 with the relatively high-viscosity coupling medium of the support portion 771, and then injecting a volume of the relatively low-viscosity, medicament-dosed coupling medium to form the medicament-containing volume 772 within the support portion 771.

In the examples illustrated in FIGS. 11 and 12, the layers of coupling medium are shown with well-defined interfaces. In practice, when layers or regions of coupling material having different compositions and/or properties are present, the interfaces between the layers or regions may be diffuse or gradual, which may further improve acoustic coupling between the layers.

FIG. 13 shows the transducer unit 100 in use with a seventh container 800. The seventh container 800 is similar to the second container 300, and therefore includes an ultrasonically-permeable closure membrane 340.

The chamber 214 of the seventh container 800 is divided into three layers 871, 872, 873. The first layer 871 is disposed adjacent to the contact membrane 212 at the proximal end of the container. The second, middle layer 872 is disposed adjacent to the first layer 871 and is separated from the first layer 871 by a first dividing membrane 881. The third layer 873 is disposed between the second layer 872 and the closure membrane 340. The second and third layers 872, 873 are separated by a second dividing membrane 882. In this way, the first and second dividing membranes 881, 882 define compartments for receiving coupling medium.

The first and third layers 871, 873 are filled with a medicament-free coupling medium. The second layer 872, which is positioned to coincide with the focusing zone of the acoustic vibrations from the transducer element 108, is filled with a coupling medium dosed with medicament. The coupling medium in the first and third layers 871, 873 may have a higher viscosity than the medicament-dosed coupling medium in the second layer 872.

The coupling medium in the first layer 871 serves to transfer acoustic energy from the output face 110 of the transducer element 108, received through the contact membrane 212, to the second layer 872, where ultrasonic-induced cavitation occurs. The first dividing membrane 881 may therefore be of the same acoustically-transparent material as the contact membrane 212 (and therefore the liner 204).

During sonophoresis, the medicament must be transported from the second layer 872 through the coupling medium in the third layer 873 to reach the skin. Accordingly, the second dividing membrane 882 may be of the same ultrasonically-penetrable material, such as a skin substitute material, as the closure membrane 340.

In this way, in the seventh container 800, the medicament is again non-uniformly distributed within the chamber 214 of the container 800, so as to minimise medicament wastage. By providing the dividing membranes 881, 882, coupling media with different physical and chemical properties can be utilised in the seventh container 800 if desired.

As noted above, in addition to ensuring good acoustic transmission from the output face of the transducer element to the coupling medium through the contact membrane, it is also desirable to ensure good acoustic transmission through the contact membrane and intimate contact between the coupling medium and the skin to allow transport of medicament into the skin. Accordingly, it is important to avoid entrapment of air at the interface between the coupling medium and the skin, and to the formation of air pockets in the coupling medium itself.

In each of the above-described examples, the chamber of the container is filled with the coupling medium and sealed in the chamber with a sealing film to preserve its sterility before the container is delivered to a user. When preparing the apparatus for use, the sealing film is removed and the distal end of the container is placed against the skin. Leakage of medicament from the chamber during this action could result in the formation of air bubbles in the medicament. However, in the above-described examples, such leakage is avoided by providing a closure membrane, or because at least the distal end of the chamber is filled with a coupling medium with sufficient viscosity to be self-supporting over the short time between removal of the sealing film and placement against the skin.

In some cases, however, it may be desirable to use a coupling medium with a relatively low viscosity and to have the coupling medium in direct contact with the skin without an intervening closure membrane.

To this end, FIG. 14 shows an apparatus in which the coupling medium can be transferred into the chamber of the container after the apparatus has been positioned against the skin.

The apparatus of FIG. 14 comprises a transducer unit 100 that corresponds to the transducer unit described above with reference to FIGS. 1 to 7, but with the housing 102 modified to include a slot 152 that extends through the wall of the housing 102 alongside the socket 134. The transducer unit 100 is used with an eighth container 900, and FIG. 14 shows the eighth container 900 fully engaged with the transducer unit 100.

The eighth container 900 is similar to the first container 200 described above. However, the chamber 914 of the eighth container 900 is not initially filled with coupling medium. Instead, a reservoir 950 is provided for holding the coupling medium outside the chamber 914 until the apparatus has been placed on the user's skin.

The reservoir 950 is connected to the chamber 914 by a fluid connection 952 that passes from the reservoir through the casing 902 and the liner 904 of the container 900 to open into the chamber 914. The slot 152 in the housing 102 of the transducer unit 100 accommodates the fluid connection 952 as the container 900 is inserted in the socket 134.

The reservoir 950 is generally tubular to define a chamber or cylinder 954 for storing the coupling medium. In this example, the coupling medium stored in the cylinder 954 does not contain medicament. A piston 956 is provided for expelling the coupling medium from the cylinder 954 into the chamber 914 of the container. The piston 956 can be driven by any suitable means, such as a user-operable button or slider coupled to the piston 956 or by a suitable drive mechanism.

A capsule 972 is suspended in the chamber 914 by a plurality of web members 960. The web members 960 are preferably made from the same acoustically-transparent material as the liner 904, so that the web members 960 do not affect acoustic transmission through the chamber. The web members 960 may be co-moulded with the liner. The capsule 972 defines a volume containing a medicament-loaded coupling medium and is encapsulated by a suitable ultrasonically-permeable membrane, for example of a skin substitute material. The capsule 972 is positioned to coincide with the location of the focusing zone of the ultrasonic output from the transducer element 108.

In use, the apparatus is placed against the skin so that the distal end of the container 900 makes contact with the skin. The piston is 956 is then driven to transfer the medicament-free coupling medium from the reservoir 950 into the chamber 914. The medicament-free coupling medium fills the remaining volume 971 of the chamber 914 to surround the capsule 972 and to provide acoustic coupling between the contact membrane 212, the capsule 972 and the skin.

As the coupling medium fills the chamber 914, air is preferably displaced from the chamber 914 by way of a suitable vent (not shown) in the liner 904 of the container 900.

To prevent unintentional flow of the coupling medium from the reservoir 950 to the chamber 914, a suitable valve (not shown) may be provided in the reservoir 950, in the fluid connection 952, or in the chamber 914 where the fluid connection 952 opens into the chamber 914. The valve prevents flow of the coupling medium unless sufficient pressure is applied by the piston 956. In one example, the valve comprises a suitable valve structure formed in the flexible material of the lining 904 of the container 900, such as a slit-type pressure-activated valve in which a slit aperture is normally held closed by the resilience of the lining 904 and opens under increased fluid pressure. A similar valve structure can also be provided to act as the vent.

In a simplified variant of the apparatus of FIG. 14, no separate capsule containing a medicament-dosed coupling medium is provided. Instead, the chamber is initially empty, and the reservoir contains medicament-dosed coupling medium that can be transferred to the chamber at the appropriate time.

FIG. 15 shows a variant of the apparatus of FIG. 14 in which the coupling medium is transferred from the reservoir 950 into the chamber 914 of the container 950 automatically once the apparatus has been positioned against the skin. In this case, the chamber 914 is initially empty, and the reservoir 954 is filled with medicament-loaded coupling medium.

The apparatus of FIG. 15 comprises a transducer unit 100 that corresponds to the transducer unit described above with reference to FIG. 14, but with the addition of two or more sensing pads 160 disposed on the distal end face of the housing 102. The sensing pads 160 are connected to control circuit (not shown) which monitors the electrical resistance between the pads 160 to detect when the pads 160, and hence the distal end of the container 900, are in contact with the user's skin.

The piston 956 of the reservoir 950 is biased by a spring 972. The piston 956 is initially locked in position by a solenoid 960 configured to operate a suitable catch mechanism (not shown). The solenoid 960 preferably forms part of the transducer unit 100 and engages with the catch mechanism upon insertion of the container 900 in the socket 134 of the transducer unit 100.

When the control circuit detects that the pads 160 are in contact with the skin, the solenoid 960 releases the piston 956, and the piston 956 is driven by the spring 972 to transfer the coupling medium into the chamber 914. The air displaced from the chamber 914 can leave the chamber 914 by way of a suitable vent.

After transfer of the coupling medium from the reservoir 950 to the chamber 914, the control circuit may then start the ultrasonic excitation of the transducer element 108.

It will be appreciated that the examples of FIGS. 14 and 15 are illustrative only, and that the reservoir could be in a different position to that illustrated. More generally, any suitable configuration of the container, the reservoir and the transducer unit could be used. It is also conceivable that the reservoir could be supplied to the user as a separate component for subsequent attachment to the container and/or the transducer unit. In this case, the container could be permanently attached to or integrated with the transducer unit, since replenishment of the coupling medium and the medicament could be achieved by exchanging the reservoir.

In the arrangements described in FIGS. 14 and 15, the coupling medium is initially contained in a reservoir that is outside of the chamber of the container. However, in other arrangements, the chamber of the container may be divided into a reservoir portion, in which the coupling medium is initially contained, and an operating portion, into which the coupling medium is transferred when the apparatus is readied for use. In such cases, a part of the transducer unit, for example the transducer element, may act as a piston to drive transfer of the coupling medium from the reservoir portion to the operating portion of the chamber.

For example, a ninth container 1000, illustrated in FIGS. 16(a) and 16(b), comprises a generally tubular casing 1002. A bore of the casing defines a chamber 1014, which is split into a proximal reservoir portion 1050 and a distal operating portion 1052. The reservoir portion 1050 and the operating portion 1052 are separated by a dividing membrane 1054. The dividing membrane 1054 is of an elastomeric material such as silicone rubber that is preferably impedance-matched to the coupling medium. The dividing membrane 1054 is perforated, and the size of the perforations is selected so that the coupling medium can pass through the dividing membrane 1054 only when under pressure.

The proximal end of the reservoir portion 1050 is closed by a contact membrane 1012, which is similar to the contact membrane of the previously-described containers. However, the contact membrane 1012 of this ninth container 1000 is adhesively attached directly to the casing 1002, with no intervening liner. A vent channel 1058 is provided in the distal end face of the casing 1002.

Although not shown in FIG. 16, the casing 1002 of the container 1000 is configured to engage with a transducer unit, for example by providing an engagement collar on the container 1000 and latching members on the transducer unit as described with reference to FIGS. 1 to 7. In this case, however, the cylindrical transducer element 1008 of the transducer unit is designed to act as a piston to displace the coupling medium from the reservoir portion 1050 of the chamber 1014 to the operating portion 1052 of the chamber 1014. Accordingly, when the container 1000 is engaged with the transducer unit, part of the casing 1002 of the container 1000 slides over the transducer element 1008 (for example, into a recess of the transducer unit) so that the transducer element 1008 is partially received in the chamber 1014 of the container 1000.

Figure 16:
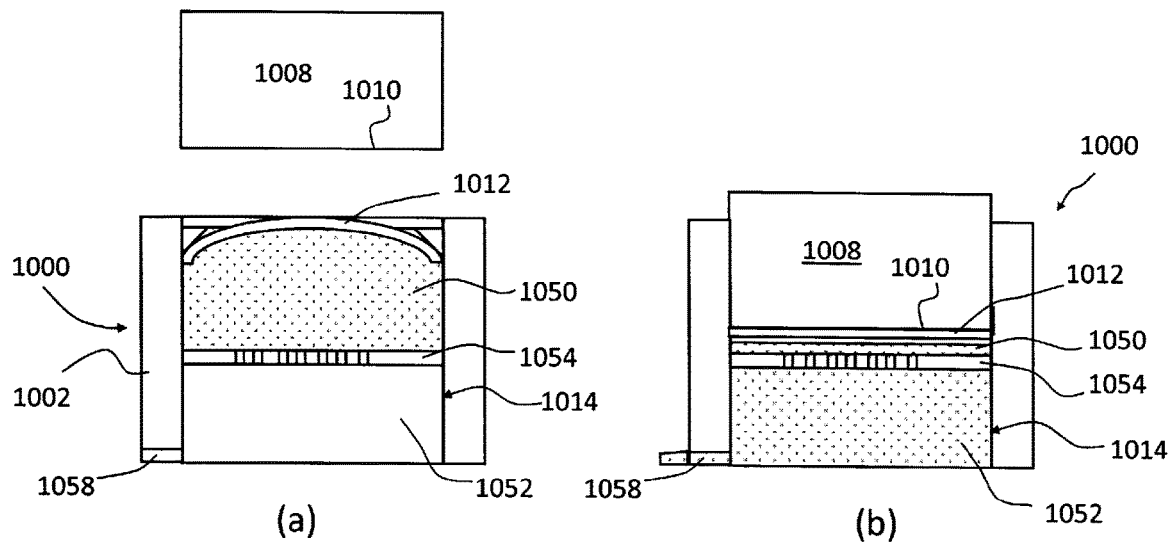

In an initial state, shown in FIG. 16(a), the contact membrane 1012 is dome-shaped and the reservoir portion 1050 of the chamber 1014 is filled with a medicament-loaded coupling medium. The operating portion 1052 of the chamber 1014 remains empty, and may be sealed with a sealing film (not shown in FIG. 16) to preserve its sterility before use.

To prepare the apparatus for use, the sealing film is removed, and the distal end of the container 1000 is placed against the skin. The transducer unit is then brought into engagement with the container 1000. The output face 1010 of the transducer element 1008 comes into the domed contact membrane 1012 and flattens the contact membrane 1012 as the container 1000 and the transducer unit are brought together to exclude air from the interface between the output face 1010 and the contact membrane 1012, as described previously with reference to FIG. 7. At the same time, the coupling medium is forced through the perforations in the dividing membrane 1054 to flow into the operating portion 1052 of the chamber 1014. The air displaced from the operating portion 1052 of the chamber 1040 can flow out of the vent channel 1058, to prevent the formation of air pockets in the coupling medium.

As the transducer element 1008 slides further into the container 1000, the contact membrane 1012 detaches from the casing 1002 and is carried on the output face 1010 of the transducer element 1008 to allowed continued movement of the transducer element 1008 into the chamber 1014.

FIG. 16(b) shows the apparatus when the container 1000 has been fully engaged with the transducer unit. In this state, the transducer element 1008 occupies the majority of the reservoir portion 1050 of the chamber 1014, and the operating portion 1052 of the chamber 1014 is now filled with coupling medium. The volume of coupling medium displaced by the transducer element 1008 is greater than the volume of the operating portion 1052 of the chamber 1014 to ensure that the operating portion 1052 of the chamber 1014 becomes completely filled with coupling medium. The excess coupling medium flows out of the vent passage 1058. The transducer element 1008 can then be energised to begin the sonophoresis process.

A variant of the apparatus of FIGS. 16(a) and 16(b), comprising a tenth container 1100, is shown in FIGS. 17(a) and 17(b). The tenth container 1100 is shown in an inverted position with respect to the previously-described containers, so that distal end of the container 1100 is uppermost In FIGS. 17(a) and 17(b).

The container 1100 comprises a generally tubular casing 1102 that defines a chamber 1114 for the coupling medium. Engagement means (not shown), such as an engagement collar, are provided to allow the container 1100 to be releasably engaged with a transducer unit. In a distal portion of the container, the thickness of the wall of the casing 1102 increases moving towards the distal end of the container, so as to define a frustoconical operating region 1152 of the chamber 1114. The operating region 1552 of the chamber 1114 opens onto the distal end face of the container 1100, and is closed by a removable sealing film 1128.

As in the apparatus of FIGS. 16(a) and 16(b), the proximal end of the chamber 1114 is closed by a dome-shaped contact membrane 1112 of acoustically-transparent material, which contacts the output face 1010 of the transducer element 1008 when the container 1100 is engaged with the transducer unit. The contact membrane 1112 is detachably affixed to the casing 1102.

In an initial state, shown in FIG. 17(a), the chamber 1114 is only partially filled with medicament-loaded coupling medium. Thus, in the initial state, the coupling medium occupies a proximal reservoir portion 1150 of the chamber 1114.

To prepare the apparatus for use, the sealing film 1128 is removed and the container 1100 is brought into engagement with the transducer unit. In this case, the container 1100 is pushed down onto the transducer element 1008 to bring the contact membrane 1112 into contact with the output face 1010 of the transducer element 1008.

As previously described, the output face 1010 flattens the initially-domed contact membrane 1112, and then the contact membrane 1112 detaches from the casing 1102 and is carried on the output face 1010 as the container 1100 is pushed further onto the transducer element 1008.

As the transducer element 1008 moves into the chamber 1114, the coupling medium is displaced into the distal operating portion 1152 of the chamber 1114, displacing the air in the chamber 1114 out of the distal end of the container. As shown in FIG. 17(b), when the container 1100 is fully engaged with the transducer unit, the operating portion 1152 of the chamber 1114 is filled with the coupling medium. The distal end of the container 1100 can then be placed against the skin to allow sonophoresis to begin.

The volume of coupling medium displaced by the transducer element 1008 is greater than the empty volume in the chamber 1114, and the excess coupling medium is pushed out of the distal end of the container 1100. The excess coupling medium on the distal end of the device can help to create an air-free interface between the coupling medium and the skin. The frustoconical shape of the operating portion 1152 of the chamber reduces wastage of medicament, as described above with reference to FIGS. 10 and 11.

Figure 17:
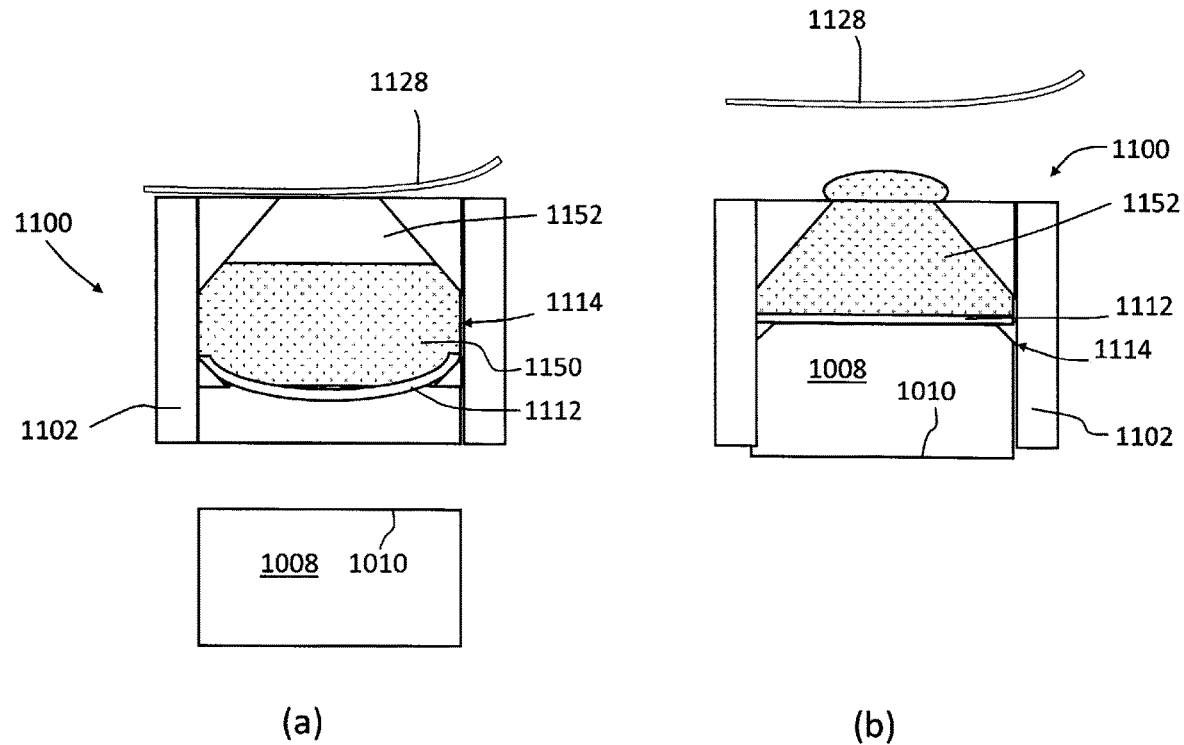

The coupling medium housed in the container of FIG. 17 may be of relatively low viscosity, so that attaching the container to the transducer unit with the distal end uppermost, as illustrated in FIG. 17, is preferred.

Figure 6:
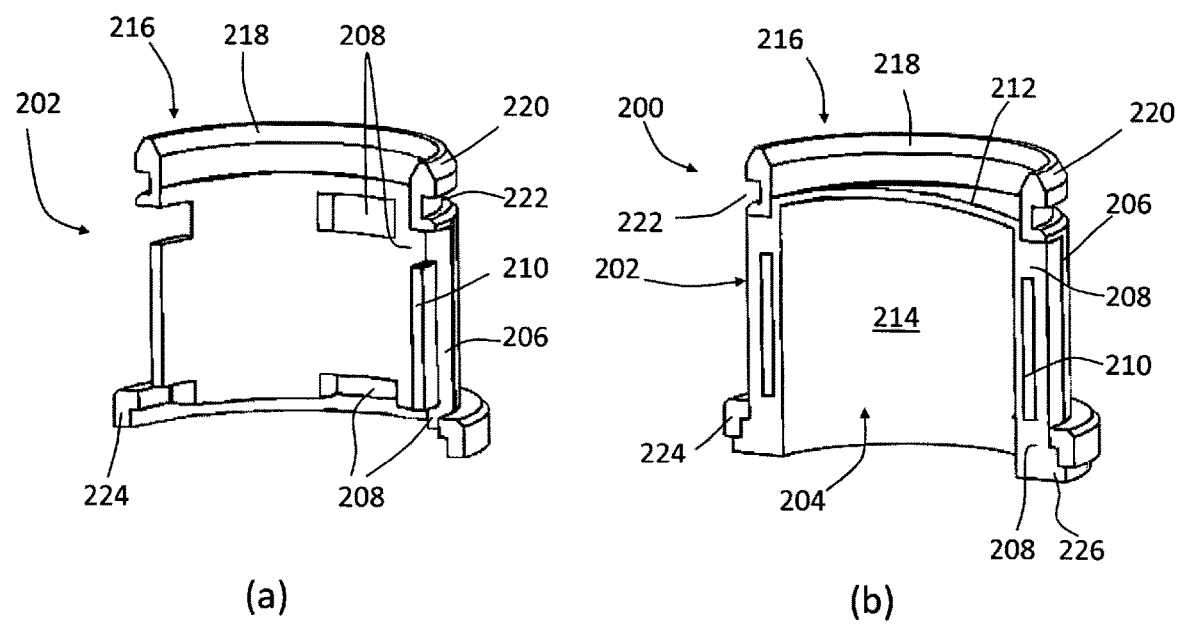

In variants of the containers shown in FIGS. 16 and 17, the container includes a liner to separate the coupling medium from the casing, and the contact membrane is part of the liner (as in, for example, the first container described with reference to FIGS. 2, 3 and 6). In this case, displacement of the membrane by the transducer element is accommodated by peeling of the liner away from the casing.

In some cases, it may be desirable to omit the contact membrane, to allow the contact medium to come into direct contact with the output face of the transducer. To this end, FIGS. 18(a) to 18(c) show the transducer unit 100 described above with reference to FIGS. 3 and 4 in use with an eleventh container 250.

Referring to FIG. 18(a), the eleventh container 250 comprises a generally tubular casing 252 that defines a generally cylindrical cavity 264 for receiving coupling medium. As in the earlier-described embodiments of the invention, the proximal end of the container 250 is provided with an engagement collar 216 for engagement with the latching members 118 of the transducer unit 100.

The chamber 264 is filled with medicament-loaded coupling medium having a relatively low viscosity. A thin proximal layer 261 of higher-viscosity coupling medium is disposed at the proximal end of the chamber 264, in contact with the coupling medium in the remainder of the chamber 264. The proximal layer 261 of coupling medium is semi-solid and self-supporting, and therefore prevents the lower-viscosity medicament-loaded coupling medium from flowing out of the proximal end of the chamber 264.

The proximal side of the proximal layer 261 provides a coupling surface 262 for contacting the output face 110 of the transducer element 108, as will be explained below. The closure layer 261 is formed into a dome shape, for example by moulding.

A removable sealing film 444 is provided to seal the proximal end of the container 250 and prevent contamination of the coupling surface 262 and the coupling medium in the chamber 264 during transport and storage of the container 250.

A closure membrane 340 extends across the distal end of the chamber 264, to contain the coupling medium in the chamber 264. As described above with reference to FIG. 8, the closure membrane 340 is of a material that is permeable when exposed to ultrasonic vibrations, such as a skin substitute material. The distal end of the container 250 is also provided with a removable sealing film 228, to prevent contamination of the closure membrane 340 before use.

To prepare the container 250 for use, the proximal sealing film 444 is removed to expose the domed coupling surface 262 of the coupling medium, as shown in FIG. 18(b). The container 250 is then inserted into the socket 134 of the transducer unit 100.

Figure 7:
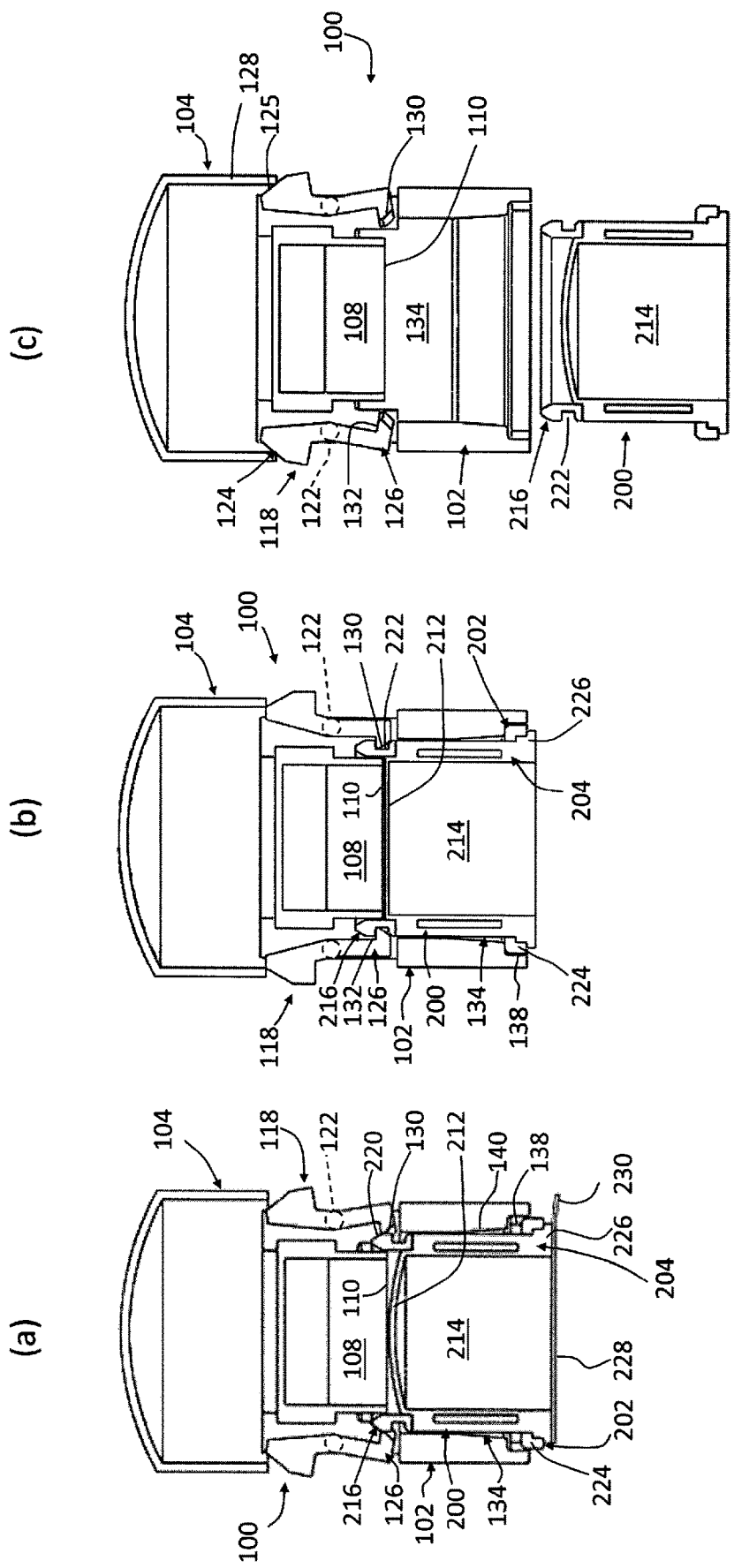
Figure 8:
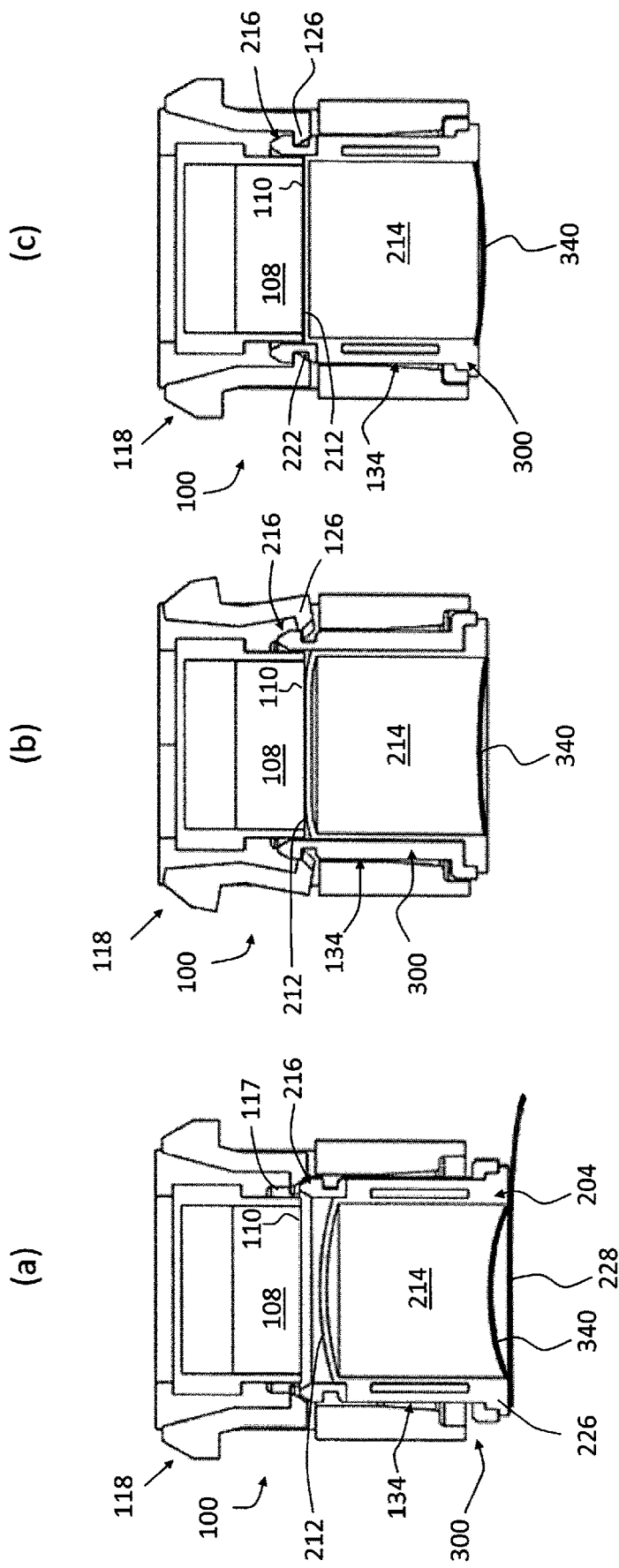

As the container 250 is moved into the socket 134, the output face 110 of the transducer element 108 contacts the coupling surface 262, causing the domed shape of the coupling surface 262 to flatten progressively to exclude air from the interface in a similar way to that described with reference to FIGS. 7 and 8 above. As the coupling surface 262 flattens, the coupling medium in the chamber 264 is displaced to cause the closure membrane 340 to deform into a convex shape.

FIG. 18(c) shows the container 250 engaged with the transducer unit 100, with the latching members 118 in engagement with the engagement collar 216 of the container 250 and the contact surface 262 of the coupling medium flat against the output face 110 of the transducer element 108. The closure membrane 340 is now domed in the distal direction to present a convex surface at the distal end of the container 250. The sealing film 228 can then be removed to allow the closure membrane 340 to be placed against the skin.

With this arrangement, good acoustic coupling is achieved between the output face 110 of the transducer element 108 and the coupling medium in the chamber 264 by virtue of the direct contact between the output face 110 and the transducer element. In particular, by omitting a contact membrane between the coupling medium and the output face 110 of the transducer element 108, acoustic transmission from the output face 110 to the coupling medium may be further improved.

In this example, the casing 252 of the eleventh container 250 is a solid-walled tube, and there is no liner to separate the coupling medium in the chamber 264 from the casing 252. However, in a variant of the eleventh container, a liner may be provided. In such a case, a casing and liner similar to those illustrated in FIG. 6 could be provided, with the contact membrane omitted.

In another variant of the eleventh container, the closure membrane 340 could be omitted or replaced with another self-supporting layer of coupling medium.

It will be appreciated that the contact membrane of the other containers described herein could conceivably be omitted to allow direct contact between the coupling medium and the transducer output face.

The first to eleventh containers described above are suitable for use with the transducer unit described with reference to FIGS. 2 to 5, or with the modified transducer units shown in FIGS. 14 and 15. It will be appreciated that various further modifications and variations of the transducer unit are possible. For instance, the transducer unit may be modified to accommodate a signal generator, control circuit, power source and/or other components. In particular, the transducer unit may be designed as a re-usable, stand-alone device that requires no connection to external components to operate once fitted with a container. An outer casing may be provided to conceal the housing and the latching members, and to support the release button.

Alternative configurations of the latching members of the transducer unit and the engagement collar of the container are possible. For example, FIG. 19 illustrates an alternative housing 102a for the transducer unit, in which three latching members 118a are provided. More generally, any suitable number of latching members could be provided, and as an alternative to the release button, the latching members could be released by a different mechanism, such as a slidable collar, or by manually disengaging each of the latching members.

Different ways of achieving releasable engagement between the container and the transducer unit are also possible. For example, the container could be attachable to the transducer unit by way of push-fit, a threaded engagement, a bayonet fitting, or by any other suitable means.

It will also be appreciated that the container design could vary considerably from the illustrated examples. In general, any suitable combination of the above-described casings, liners, contact membranes, closure membranes, dividing membranes, sealing films, chamber shapes and medicament distributions could be selected for a given application.

In another variant of the apparatus, the transducer unit includes an array of transducer elements, and the container has a corresponding array of chambers to cooperate with the transducer elements. One potential advantage of such an arrangement is that, for an equivalent treatment area diameter and output intensity, an array of transducers occupies a smaller volume and has a lower profile than a single transducer.

One example is illustrated in FIG. 20, in which the housing 102 of the transducer unit 100 of FIGS. 2 to 5 is shown approximately to scale alongside a housing 1220 of a transducer unit of equivalent capability comprising five smaller transducer elements, arranged in a pentagonal array. As can be seen, the diameter of the housing 1220 of the transducer array is approximately the same as the housing 102 of the single transducer variant. However, the height of the housing 1220 of the array and the volume occupied is substantially smaller.

FIGS. 21(a) to 21(c) show a five-element transducer array unit 1200 in use with a corresponding container 1300. FIG. 21(a) shows the transducer unit 1200 and the container 1200 separately.

Figure 21:
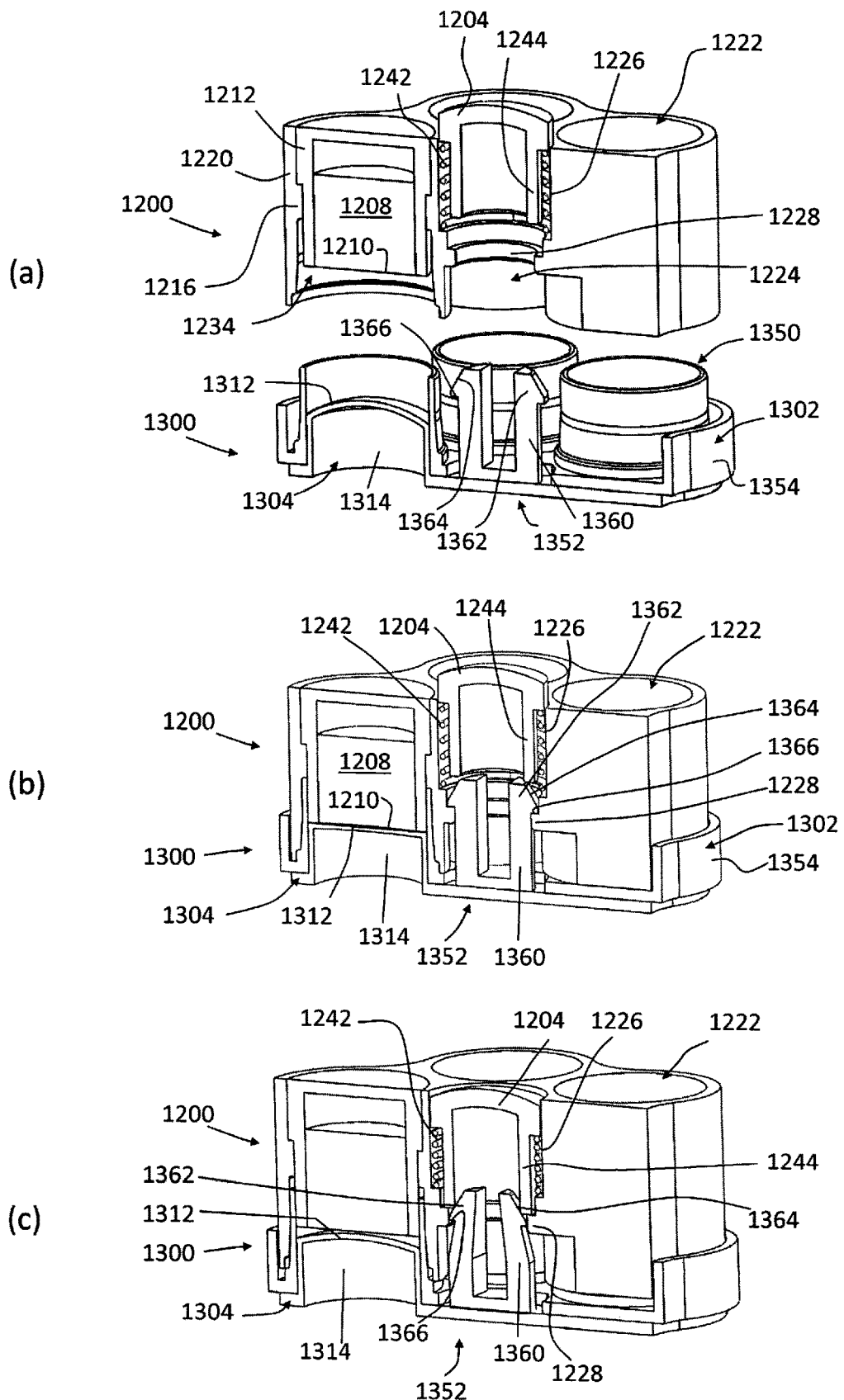

The transducer unit comprises the housing 1220 of FIG. 20, which has five tubular transducer holder segments 1222 (only three of which are visible in FIG. 21). The transducer holder segments 1222 are arranged in parallel to one another and are spaced at equal angles around a central hub 1224 to form a pentagonal array.

Each transducer holder segment 1222 has a similar internal shape to the housing body 102 of the single-element transducer unit shown in FIGS. 2 to 5, and accepts a transducer element 1208 in a transducer casing 1212. A shoulder 1214 of each transducer casing 1212 abuts a collar 1216 of the corresponding transducer holder segment 1222 to locate the casing 1212 in the bore of the tubular segment 1222.

The hub 1224 of the housing comprises a central space that includes a cylindrical button recess 1226 that extends distally from the proximal end of the housing and a collar 1228 disposed at the distal end of the recess 1226. The collar 1228 is spaced from the distal end face of the housing 1220 and forms part of an engagement means to engage the container 1300 with the transducer unit 1200. The button recess 1226 houses a cap-shaped release button 1204 and a biasing spring 1242 arranged to bias the release button 1242 in the proximal direction.

The container 1300 comprises a casing 1302 and a liner 1304 attached to the casing 1302 by overmoulding, adhesive or other suitable means. The container 1300 includes five generally tubular sub-containers 1350 (only three of which are shown in FIG. 21) arranged around a central connecting boss 1352 of the casing 1302. The casing also includes an upstanding peripheral wall 1354.

Each sub-container 1350 is similar to the first container 200 described above with reference to FIGS. 2, 3 and 6. The liner 1304 is acoustically transparent and is shaped to define a chamber 1314 of each sub-container 1350. The liner 1303 is formed into dome-shaped contact membranes 1312 that close the proximal end of each chamber 1314.

Each chamber 1314 is filled with a medicament-loaded coupling medium. The distal end of each chamber 1314 may be open to allow direct contact between the coupling medium and the skin in use, as shown in FIG. 21, or alternatively the distal end of each chamber 1314 may be closed by a closure membrane, as in the second container described above with reference to FIG. 8. In either case, a removable sealing film (not shown) can be affixed to the distal face of the container 1300 to preserve the sterility of the container 1300 and its contents before use.

The boss 1352 of the casing 1302 includes a pair of proximally-extending latching members in the form of latching arms 1360. Each arm 1360 includes a head portion 1362 with a ramped proximal face 1364 and a laterally-extending distal face 1366.

Each transducer holder segment 1222 includes a socket 1234 for receiving a respective sub-container 1350 of the container 1300. In use, the container 1300 can be brought into engagement with the transducer unit 1200 by sliding each of the sub-containers 1350 into the respective socket 1234, to bring each of the contact membranes 1312 into contact with a respective output face 1210 of a transducer element 1208. The output faces 1210 flatten the initially-domed contact membranes 1312 to eliminate air from the respective interfaces.

As the container 1300 and the transducer unit 1200 are brought together, the ramped proximal faces 1364 of the latching arms 1360 come into contact with the collar 1228 of the hub 1224 of the transducer unit housing 1220. This causes the arms 1360 to bend inwardly towards one another as the collar 1228 rides over the ramped faces 1364. Once the head portions 1362 of the latching arms 1360 have passed the collar 1228, the arms 1360 spring outwards.

FIG. 21(b) shows the container 1300 fully engaged with the transducer unit 1200 so that the apparatus is ready to be placed against the skin. The distal faces 1366 of the head portions 1362 of the arms 1360 cooperate with the collar 1228 to prevent separation of the container 1300 from the transducer unit 1200. In this way, the collar 1228 provides an engagement formation for cooperation with the latching arms 1360. The peripheral wall 1354 of the casing 1302 shrouds the distal end of the transducer unit 1200.

The release button 1204 is arranged to cooperate with the engagement arms 1360 to release the container 1300 from the transducer unit 1200 after use. As shown in FIG. 21(c), when the release button 1204 is moved in the distal direction, against the biasing force of the spring 1242, a tubular collar 1244 of the button 1204 pushes against the ramped faces 1364 of the arms 1360. This causes the arms 1360 to bend towards one another, allowing the head portions 1362 to clear the collar 1228, and also serves to push the arms 1360 in the distal direction to eject the container 1300 from the transducer unit 1300.

Other arrangements for attaching and releasing the container 1300 from the transducer unit 1200 may be used. For example, the transducer unit and the container could both have a circular outer periphery, and a captive threaded collar provided on either the transducer unit or the container to engage with a threaded part of the other component.

It will be appreciated that the apparatus of FIG. 21 could be modified to adopt any suitable features of the single-transducer variants described with reference to FIGS. 2 to 19.

Furthermore, whilst the apparatus shown in FIG. 21 utilises an array of five transducer elements, any suitable number of transducer elements could be provided. For example, arrangements with an array of three, four or six transducer elements may be used.

The above-described examples are designed for ultrasound-enhanced medicament delivery using sonophoresis. However, it will be understood that the same principles could be applied in other applications that require a coupling medium in liquid or gel to be positioned between a transducer and a patient's skin. For example, the transducer could provide light, thermal, acoustic, mechanical, electrical or other stimulus to the coupling medium and/or to the skin for therapeutic or other applications.

The above-described arrangements are examples only and many further variants and modifications are possible without departing from the scope of the invention as defined in the appended claims.

The invention claimed is:

1. A container for containing a coupling medium for transdermal delivery of a medicament using a transducer unit having a transducer with an output face, the container comprising:
    a chamber for receiving the coupling medium,
        the chamber having a proximal end and a distal end; and
    a contact surface for contacting the output face of the transducer,
        the contact surface having a domed shape which covers extends across the proximal end of the chamber such that an apex of the contact surface bulges in a proximal direction when the chamber is filled with the coupling medium, and
        the contact surface being flexible such that the apex of the contact surface flattens as it contacts the output face of the transducer;
    wherein the container is attachable to the transducer unit and is arranged such that, upon attachment of the container to the transducer unit, an acoustic coupling for ultrasound transmission is formed between the output face of the transducer and the contact surface.

2. The container according to claim 1, arranged such that a substantially air-free coupling is formed between the output face of the transducer and the contact surface upon attachment of the container to the transducer unit.

3. The container according to claim 1, wherein the contact surface is deformable to conform to the output face of the transducer upon attachment of the container to the transducer unit.

4. The container according to claim 1, wherein the contact surface is arranged such that a contact area between the contact surface and the output face increases to exclude air during attachment of the container to the transducer unit.

5. The container according to claim 1, comprising a removable seal arranged to cover the contact surface before attachment of the container to the transducer unit.

6. The container according to claim 1, wherein the contact surface is disposed at a proximal end of the chamber, and wherein a distal end of the chamber is closed by a self-supporting layer of the coupling medium.

7. The container according to claim 1, wherein the container is releasably attachable to the transducer unit.

8. The container according to claim 1 for use with the transducer unit comprising a plurality of transducers, wherein the container comprises a corresponding plurality of chambers, each chamber having a respective contact surface arranged to contact a respective output face of an associated one of the plurality of transducers.

9. The container according to claim 1, wherein the chamber contains the coupling medium, and wherein the contact surface is in contact with a surface of the coupling medium.

10. The container according to claim 9, comprising a self-supporting layer of coupling medium disposed at a proximal end of the chamber, and wherein the contact surface is in contact with a proximal surface of the self-supporting layer.

11. The container according to claim 1, wherein the contact surface is disposed at a proximal end of the chamber, and wherein a distal end of the chamber is closed by a closure membrane.

12. The container according to claim 11, wherein the closure membrane comprises a skin substitute material.

13. The container according to claim 1, wherein the chamber has a non-uniform diameter.

14. The container according to claim 13, wherein the diameter of the chamber decreases with distance from the contact membrane over at least a portion of the chamber.

15. The container according to claim 1, wherein attachment of the container to the transducer unit causes displacement of the coupling medium from a reservoir portion of the chamber to an operating portion of the chamber.

16. The container according to claim 15, wherein the reservoir portion of the chamber and the operating portion of the chamber are separated by a separator membrane.

17. The container according to claim 15, wherein the transducer of the transducer unit displaces the coupling medium from the reservoir portion to the operating portion.

18. The container according to claim 1, comprising a reservoir external to the chamber for holding the coupling medium, and transfer means for transferring the coupling medium to the chamber.

19. The container according to claim 18, wherein the transfer means comprises a piston disposed in the reservoir.

20. The container according to claim 18, wherein the container or the transducer unit comprises skin contact detection means, and wherein the transfer means is operable upon detection of skin contact by the skin contact detection means.

21. The container according to claim 1, further comprising engagement means for locking the container to the transducer unit.

22. The container according to claim 21, wherein the engagement means is arranged such that, upon attachment of the container to the transducer unit, the engagement means locks the container to the transducer unit once a coupling between the output face of the transducer and the contact surface has been formed.

23. The container according to claim 21 wherein, upon engagement of the engagement means with the container, the contact surface is pressed against the output face of the transducer.

24. The container according to claim 21, wherein the engagement means comprises an engagement formation for engagement with one or more latching members of the transducer unit.

25. The container according to claim 24, wherein the engagement means comprises one or more latching members for engagement with an engagement formation of the transducer unit.

26. The container according to claim 1, comprising a contact membrane, wherein the contact surface comprises a surface of the contact membrane.

27. The container according to claim 26, wherein the chamber is defined at least in part by the contact membrane.

28. The container according to claim 26, wherein the contact membrane is arranged to elastically deform upon attachment of the container to the transducer unit.

29. The container according to claim 26, wherein the contact membrane impedance is matched to an impedance of the coupling medium.

30. The container according to claim 26, wherein the contact membrane is of an elastomeric material.

31. The container according to claim 30, wherein the contact membrane comprises a silicone material.

32. The container according to claim 26, comprising a contact medium to couple the contact membrane to the output face of the transducer upon attachment of the container to the transducer unit.

33. The container according to claim 32, comprising a removable seal arranged to contain the contact medium between the contact membrane and the seal.

34. The container according to claim 26, further comprising a casing.

35. The container according to claim 34, wherein the contact membrane is supported by the casing.

36. The container according to claim 34, wherein the casing is of a rigid plastics material.

37. The container according to claim 34, comprising a liner for separating the coupling medium from the casing.

38. The container according to claim 37, wherein the contact membrane is part of the liner.

39. The container according to claim 37, wherein at least one portion of the casing extends through the liner to attach the liner to the casing.

40. The container according to claim 1, wherein the chamber contains a medicament-containing coupling medium.

41. The container according to claim 40, wherein the medicament-containing coupling medium substantially fills the chamber.

42. The container according to claim 41, wherein the medicament-containing coupling medium is contained in a volume within the chamber.

43. The container according to claim 42, wherein a remaining volume of the chamber contains a medicament-free coupling medium.

44. The container according to claim 42, wherein the medicament-containing coupling medium is contained in a capsule suspended in the chamber.

45. The container according to claim 42, wherein the medicament-containing coupling medium is disposed in a layer in the chamber.

46. The container according to claim 42, comprising at least one dividing membrane for containing the medicament-containing coupling medium within the volume.

* * * * *